(12) United States Patent
Ow

(10) Patent No.: US 11,806,272 B2
(45) Date of Patent: Nov. 7, 2023

(54) DEVICES AND METHODS FOR TREATING OBSTRUCTIVE BREATHING DISORDERS

(71) Applicant: Randall Ow, Loomis, CA (US)

(72) Inventor: Randall Ow, Loomis, CA (US)

(*) Notice: Subject to any disclaimer, the term of this patent is extended or adjusted under 35 U.S.C. 154(b) by 186 days.

(21) Appl. No.: 17/191,019

(22) Filed: Mar. 3, 2021

(65) Prior Publication Data

US 2021/0275346 A1 Sep. 9, 2021

Related U.S. Application Data

(60) Provisional application No. 62/984,792, filed on Mar. 4, 2020.

(51) Int. Cl.
*A61F 5/56* (2006.01)
*A61M 16/20* (2006.01)

(52) U.S. Cl.
CPC ............ *A61F 5/566* (2013.01); *A61M 16/20* (2013.01); *A61M 2205/073* (2013.01)

(58) Field of Classification Search
CPC .. A61F 5/00; A61F 5/3756; A61F 5/56; A61F 5/566; A61F 2/00; A61F 2/02; A61M 16/0495; A61M 16/20; A61M 2205/07; A61M 2205/071; A61M 2205/073; A61B 17/00; A61B 17/04; A61B 17/24; A61B 17/68; A61B 17/84; A61B 2017/24;
(Continued)

(56) References Cited

U.S. PATENT DOCUMENTS 6,408,851 B1 6/2002 Karell
6,679,257 B1 1/2004 Robertson et al.
(Continued)

FOREIGN PATENT DOCUMENTS

EP 2617460 A2 7/2013
FR 2942954 A1 9/2010
(Continued)

OTHER PUBLICATIONS

Bradford, Alina, The Tongue: Facts, Function & Diseases, Oct. 15, 2015 [retrieved on Jul. 18, 2023]. Retrieved from the internet, <URL: https://www.livescience.com/52362-tongue.html (Year: 2015).*
(Continued)

*Primary Examiner* — Ophelia A Hawthorne
*Assistant Examiner* — Gina McCarthy
(74) *Attorney, Agent, or Firm* — Aurora Consulting LLC; Ashley Sloat

(57) ABSTRACT

Described herein are devices and methods of treating obstructive breathing disorders in a patient. A method may include: attaching an anchor to a dorsal region of a tongue body; applying an external force to the tongue body; and adjusting a magnitude of the external force. In some embodiments, the magnitude of the external force is adjustable across multiple levels based on one or more of: patient comfort, desired therapeutic effect, or patient wake or sleep state. In some embodiments, at least a portion of the external force is directed along an anterior direction. In some embodiments, the external force causes at least one of the following actions: anterior displacement of a portion of the posterior tongue during sleep or reducing posterior displacement of a portion of the tongue during sleep.

25 Claims, 33 Drawing Sheets

(58) Field of Classification Search
CPC . A61B 2017/28; A61B 13/00; Y10S 602/902; A61N 1/05
See application file for complete search history.

(56) References Cited

U.S. PATENT DOCUMENTS

| | | | |
|---|---|---|---|
| 6,997,186 | B2 | 2/2006 | Robertson et al. |
| 7,073,506 | B2 | 7/2006 | Robertson et al. |
| 7,703,460 | B2 | 4/2010 | Conrad et al. |
| 7,845,357 | B2 | 12/2010 | Buscemi et al. |
| 8,371,307 | B2 | 2/2013 | Hirotsuka et al. |
| 8,556,797 | B2 | 10/2013 | Weadock et al. |
| 9,421,073 | B2 | 8/2016 | Makower et al. |
| 10,195,010 | B2 | 2/2019 | Sanders |
| 10,736,771 | B2 | 8/2020 | Sanders et al. |
| 2002/0056462 | A1* | 5/2002 | Conrad .............. A61F 5/566 128/898 |
| 2005/0004417 | A1 | 1/2005 | Nelson et al. |
| 2007/0163603 | A1 | 7/2007 | Sikora |
| 2008/0053461 | A1* | 3/2008 | Hirotsuka .......... A61F 5/566 128/200.24 |
| 2008/0066765 | A1* | 3/2008 | Paraschac .......... A61F 5/56 128/848 |
| 2008/0208265 | A1* | 8/2008 | Frazier ............... A61F 5/566 606/232 |
| 2011/0100377 | A1 | 5/2011 | Weadock et al. |
| 2012/0022389 | A1* | 1/2012 | Sanders ............. A61N 1/05 600/533 |
| 2013/0180528 | A1* | 7/2013 | Zhou ................. A61F 2/00 128/848 |
| 2017/0020506 | A1 | 1/2017 | Feezor et al. |
| 2018/0168850 | A1* | 6/2018 | Thompson .......... A61F 5/566 |
| 2019/0175169 | A1 | 6/2019 | van der Burg et al. |
| 2020/0069320 | A1* | 3/2020 | Sanders ............. A61F 5/566 |
| 2020/0305859 | A1 | 10/2020 | Hendricks et al. |

FOREIGN PATENT DOCUMENTS

| | | |
|---|---|---|
| WO | 2010051195 A1 | 5/2010 |
| WO | 2011068952 A1 | 6/2011 |
| WO | 2013182893 A2 | 12/2013 |
| WO | 2017135907 A1 | 8/2017 |
| WO | 2018200063 A1 | 11/2018 |
| WO | 2020142519 A1 | 7/2020 |

OTHER PUBLICATIONS

Watson, Stephanie, What Causes Swollen Taste Buds, Mar. 7, 2019 [online], [retrieved on Feb. 28, 2023]. Retrieved from the Internet <URL: https://www.healthline.com/health/swollen-taste-buds (Year: 2019).*

Filifan, Reham et al., Double lingual frenulum: a case report, Jul. 26, 2020, Journal of Medical Case Reports, 14, Article No. 116, [online], [retrieved on Mar. 1, 2023]. Retrieved from the Internet <URL: https://jmedicalcasereports.biomedcentral.com/articles/10.1186/s13256-020-02440-7#:~:text=Walker% (Year: 2020).*

Sleep Lab, 2023, [online], [retrieved Mar. 1, 2023}. Retrieved from the Internet <URL: https://www.madison-health.com/sleeplab.php (Year: 2023).*

E. Gillis et al., article entitled "A novel implantable device for a minimally invasive surgical treatment of obstructive sleep apnea: design and preclinical safety assessment," Nature and Science of Sleep, Jul. 20, 2016, 2016:8, p. 249-258, Dovepress. (10 pages).

V. Pavelec et al., article entitled "A novel implantable device for the treatment of obstructive sleep apnea: clinical safety and feasibility," Nature and Science of Sleep, May 4, 2016, 2016:8, p. 137-144, Dovepress. (8 pages).

Y Muranishi et al., article entitled "A novel suction-based lung-stabilizing device for video-assisted thoracoscopic surgical procedures," Journal of Thoracic Disease, 2018; 10(2), p. 1081-1083. (3 pages).

AIRLIFT®, Adjustable Hyoid Suspension Procedure Guide, Siesta Medical, Inc., 2020. (2 pages).

AIRLIFT®, Hyoid Suspension, Siesta Medical, Inc., 2020. (2 pages).

AIRLIFT®, DISE, Hypopharyngeal Collapse & the AIRLIFT Airway Effect, Siesta Medical, Inc. (2 pages).

AIRvance® Bone Screw System, Tongue and Hyoid Suspension, Medtronic. (48 pages).

AIRvanceTM System for Obstructive Sleep Apnea from Medtronic, Medtronic. (4 pages).

AveoTSD® Anti-Snoring Device. (1 page).

L Mu et al., article entitled "Human Tongue Neuroanatomy: Nerve Supply and Motor Endplates," Clin Anat., Oct. 2010, 23(7), p. 777-791. (27 pages).

LinguaFlex Tongue Retractor (LTR) for the Treatment of OSA and Snoring in Adults, Linguaflex, Inc., ClinicalTrials.gov Identifier: NCT04129229, Oct. 16, 2019. (6 pages).

L Mu et al., article entitled "Sensory Innervation of the Human Soft Palate," The Anatomical Record, 2018, 301: p. 1861-1870, Wiley Periodicals, Inc. (10 pages).

EncoreTM Suspension System, Hyoid & Tongue Suspension, Siesta Medical, Inc. (1 page).

D McGeorge, The "Niplette": an instrument for the non-surgical correction of inverted nipples, British Journal of Plastic Surgery, 47, 1994, p. 46-49. (4 pages).

International Search Report dated Jun. 29, 2022 re PCT/US22/18650 (4 pages).

Written Opinion dated Jun. 29, 2022 re PCT/US22/18650 (5 pages).

* cited by examiner

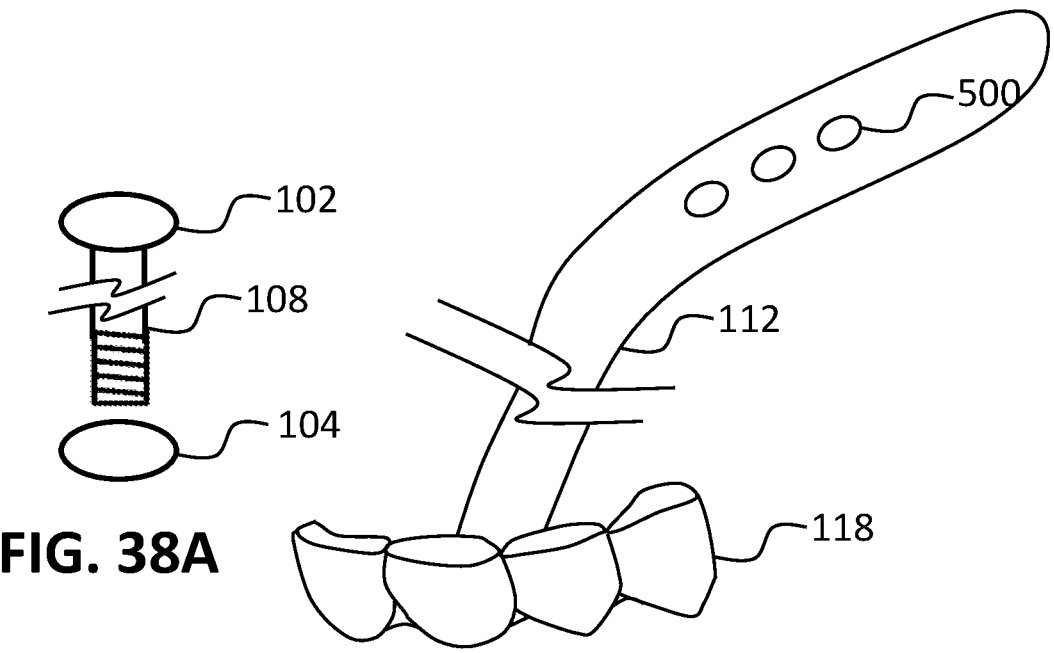
FIG. 38A
FIG. 38B
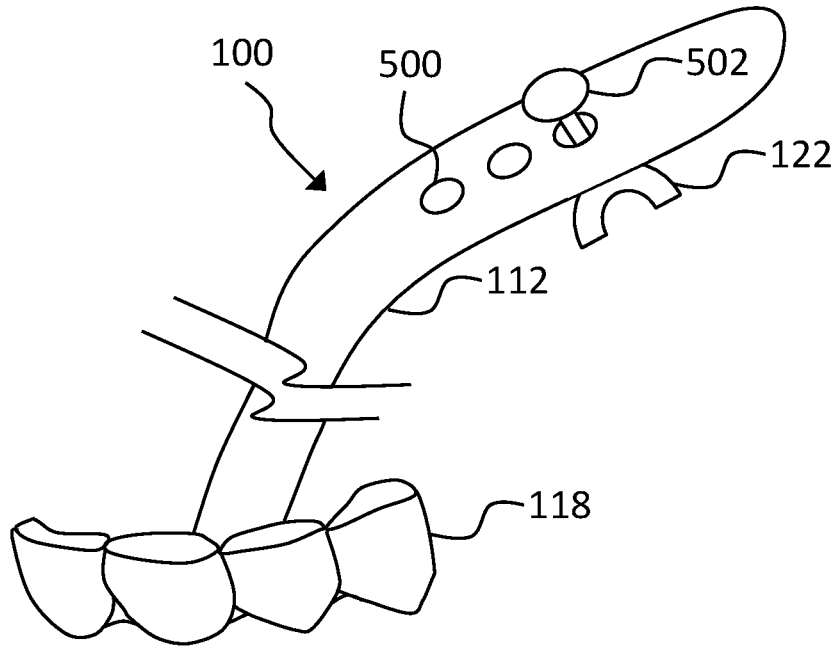
FIG. 38C

DEVICES AND METHODS FOR TREATING OBSTRUCTIVE BREATHING DISORDERS

CROSS-REFERENCE TO RELATED APPLICATIONS

This application claims the priority benefit of U.S. Provisional Patent Application Ser. No. 62/984,792, filed Mar. 4, 2020, which is herein incorporated by reference in its entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of otolaryngology, and more specifically to the field of obstructive breathing disorders. Described herein are devices and methods for treating obstructive breathing disorders.

BACKGROUND

Sleep apnea is a common disorder affecting more than 15 million adults in the U.S. Patients with sleep apnea experience stopped or shallow breathing when they sleep. The most common type of sleep apnea is obstructive sleep apnea (OSA). The airway of patients with OSA collapses—during sleep. These patients often snore loudly. Since the patient's sleep is interrupted throughout the night, they are often drowsy during daytime. Further, patients with sleep apnea often experience severe fatigue and are very motivated for a solution to their condition. Further, many OSA sufferers have other medical problems such as hypertension, cardiac disease, type 2 diabetes, stroke, and depression because of their OSA. The prevalence of OSA is expected to continue to rise because of the rising obesity rates in the United States.

Treatments include lifestyle changes such as weight loss and avoiding alcohol before sleeping, mouthpieces, breathing devices, and continuous positive airway pressure (CPAP). Patients who do not tolerate or are not helped by these methods may be offered surgery on the nose and/or throat. A major limitation of surgery is the inability to directly address the collapsing tongue base. The tongue base is suspected to be the primary site of obstruction, but surgery on the tongue base is limited due to the serious complications that can occur with invasive procedures on the tongue base itself. Complications include tongue paralysis, permanent swallowing changes, loss of taste and life-threatening bleeding and swelling. Less dangerous surgeries include palatoplasty, hyoid suspension, genioglossal advancement and hypoglossal nerve implantation. But these surgeries are invasive, expensive, and cause a substantial and permanent change to the anatomy. Further, the effect of these surgeries cannot be adjusted after the actual procedure.

Accordingly, there is a large unmet need for a treatment for sleep apnea, especially OSA, that is minimally invasive, easy to perform and does not cause significant alteration of the patient's anatomy, such that it can be easily reversed or adjusted if needed.

SUMMARY

One aspect of the present disclosure is directed to a method of treating obstructive breathing disorders in a patient. In some embodiments, the method may include attaching an anchor to a dorsal region of a tongue body; applying an external force to the tongue body through the anchor; and adjusting a magnitude of the external force. In some embodiments, the magnitude of the external force is adjustable across multiple levels based on one or more of: patient comfort, desired therapeutic effect, or patient wake or sleep state. In some embodiments, at least a portion of the external force is directed along an anterior direction. In some embodiments, the external force causes at least one of the following actions: anterior displacement of a portion of the posterior tongue during sleep or reducing posterior displacement of a portion of the tongue during sleep.

In some embodiments, attaching includes positioning the anchor in an anterior two thirds portion of the tongue body. In some embodiments, attaching includes positioning the anchor anterior to a circumvallate papillae of the tongue body. In some embodiments, attaching includes positioning the anchor about 1 cm to about 3 cm posterior to a tip of the tongue body.

In some embodiments, attaching includes applying a suction force to couple the anchor to the dorsal region of the tongue body.

In some embodiments, attaching includes inserting an anchor through a portion of the dorsal region of the tongue body.

In some embodiments, the forces are about 0.01N to about 5N.

In some embodiments, the method further includes reducing a force on the tongue body to zero force when the patient is at least partially upright or awake.

In some embodiments, applying the external force occurs when the patient is lying down or asleep.

In some embodiments, the method further includes simulating a sleep state and attaching a temporary anchor to the dorsal region of the tongue body before attaching the anchor to the dorsal region of the tongue body.

In some embodiments, the method further includes generating a positive airway pressure to further create an anterior displacement force on one or more of: a tongue region or a soft palate region.

Another aspect of the present disclosure is directed to a method of treating obstructive breathing disorders in a patient. In some embodiments, the method includes providing a device comprising a suction anchor reversibly attached to a dorsal region of a tongue body; attaching a suction anchor of the device to the dorsal region of the tongue body; applying an external force to the tongue body; and adjusting a magnitude of the external force.

In some embodiments, the device further includes: a vacuum generating element defining a chamber fluidly connected to a lumen defined by an elongate member in fluid communication with the suction anchor; a valve having an open state and a closed state, such that, in the open state, at least a partial vacuum force is applied to the suction anchor; and an external anchor configured to couple the device to a body portion of the patient. Although, as one of skill in the art will appreciate, any of the devices described herein may be used with this method.

In some embodiments, the magnitude of the external force is adjustable across multiple levels based on one or more of: patient comfort, desired therapeutic effect, or patient wake or sleep state.

In some embodiments, at least a portion of the external force is directed along the anterior direction.

In some embodiments, the external force causes at least one of the following actions: anterior displacement of a portion of the posterior tongue during sleep or reducing posterior displacement of a portion of the tongue during sleep.

In some embodiments, the vacuum generating element includes a syringe.

In some embodiments, the elongate member includes a flexible strap that defines one or more apertures that are configured to be coupled to the suction anchor.

In some embodiments, the device further includes a secondary connector to prevent decoupling of the suction anchor from the device when the elongate member fails.

In some embodiments, the method further includes identifying one or more anatomical regions responsible for obstructing an upper airway of the patient.

In some embodiments, the method further includes adjusting the anchor based on said identifying.

Another aspect of the present disclosure is directed to a method of treating obstructive breathing disorders in a patient. In some embodiments, the method includes attaching an anchor to a dorsal region of a tongue body; applying an external force to the tongue body through the anchor; and adjusting a magnitude of the external force.

In some embodiments, the magnitude includes a first magnitude when the patient is at least partially upright, a second magnitude when the patient is lying down, and one or more intermediate magnitudes, between the first and second magnitudes, based on one or more of: patient comfort, desired therapeutic effect, or patient wake or sleep state.

In some embodiments, at least a portion of the external force is directed along an anterior direction.

In some embodiments, the external force causes at least one of the following actions: anterior displacement of a portion of the posterior tongue during sleep or reducing posterior displacement of a portion of the tongue during sleep.

In some embodiments, the method further includes tapering the second magnitude of the external force over time to wean the patient from the treatment.

In some embodiments, the first magnitude of the external force is substantially zero.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

FIG. 38A shows one embodiment of an anchor of a multi-level adjustable device.

FIG. 38B shows one embodiment of a multi-level adjustable device using a tongue anchor.

FIG. 38C shows another embodiment of a multi-level adjustable device using a surface anchor.

Figure 1:
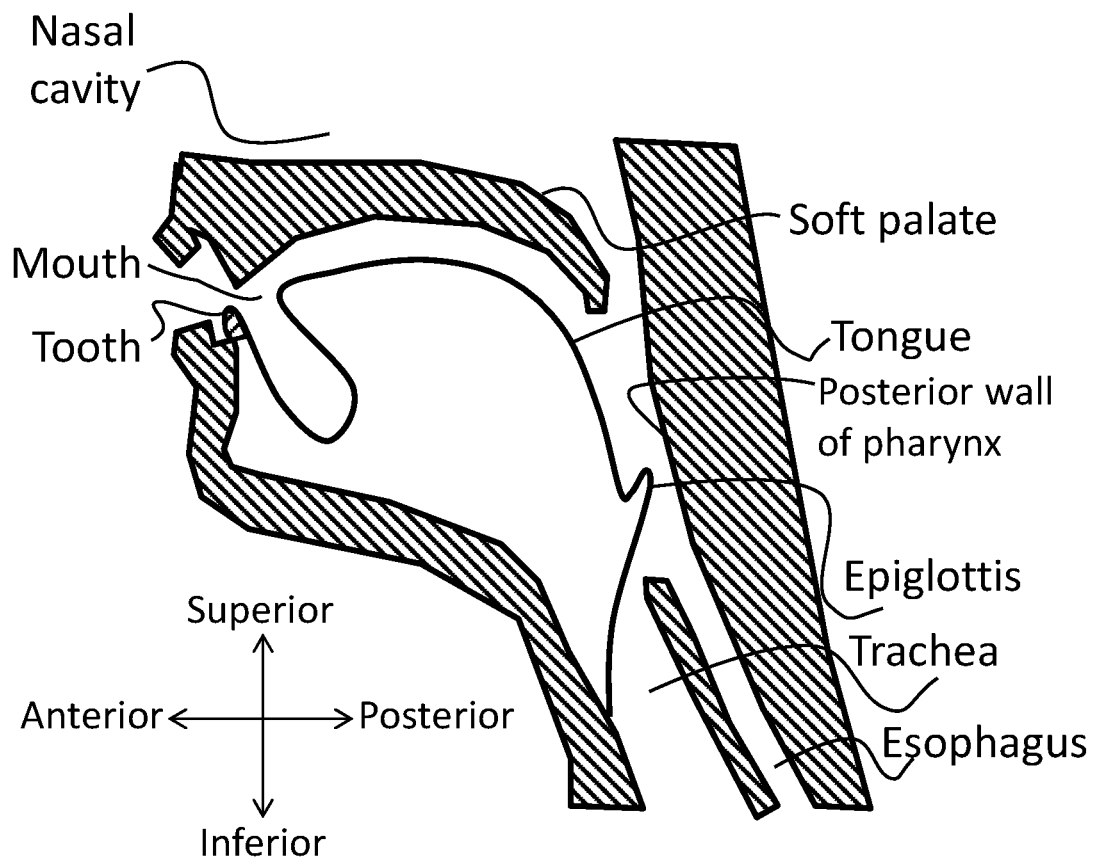
FIG. 1 shows a section through a human head showing the general anatomy and the convention used to indicate direction, as used herein.
Figure 2:
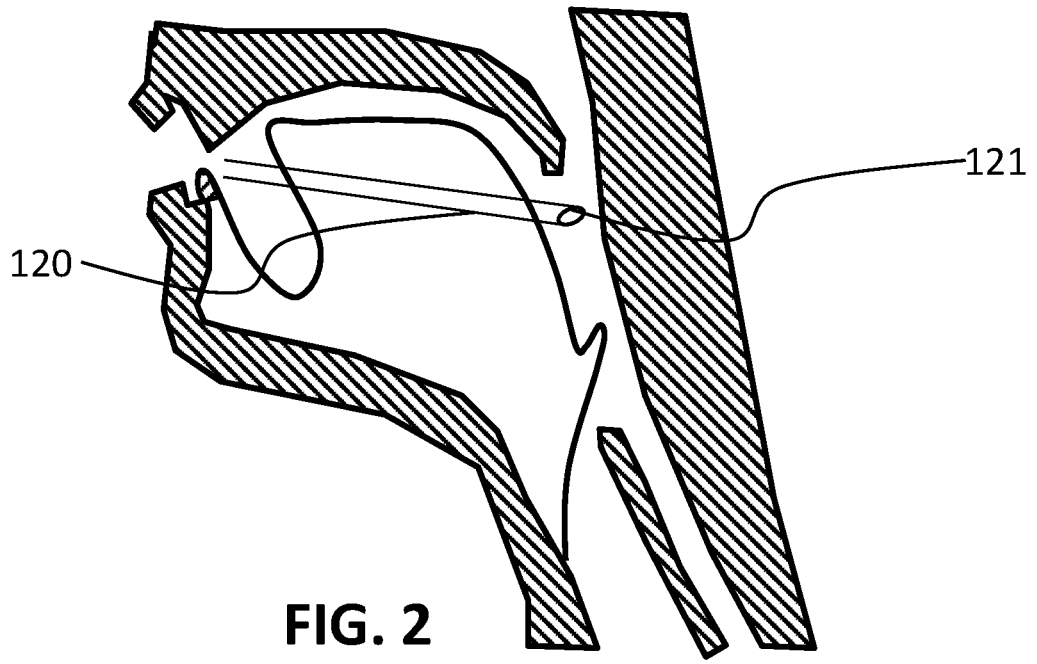
FIG. 2 shows one embodiment of a method of passing a penetrating element through a tongue.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

In general, the devices shown and described herein may be configured to retract or displace a tissue. For example, the devices and methods shown and described herein may be used to displace a tongue, retract an organ or displace it from a surgical field, maintain a bodily structure in an open or closed position, etc. Such displacement or retraction may be temporary or permanent.

Further, in general, as described herein, an anchor, for example a tissue anchor, may anchor to the tissue via one or more tissue penetrating elements. Additionally, or alternatively, a tissue anchor may pass through the tissue in a first collapsed configuration and may expand to a second expanded configuration during deployment, such that the second expanded configuration is sized and shaped such that it is retained on a surface of the tissue. Additionally, or alternatively, a tissue anchor may be secured to an elongate member after the elongate member is passed through the tissue, such that the anchor is snapped, screwed, threaded, etc. onto the elongate member or the elongate member is passed through and retained (permanently, adjustably, or removably), at least partially, by the tissue anchor. Additionally, or alternatively, a tissue anchor may be retained via suction, magnetic, or electromechanical means, as described elsewhere herein.

In general, any of the devices described herein may be adjusted across multiple levels. For example, force exerted on the tongue by the device may be adjusted to different levels to achieve different degrees of effect or displacement. In one embodiment, a first magnitude of force is applied when the patient is at least partially upright, and a second magnitude of force is applied when the patient is lying down. In some embodiments, one or more intermediate magnitudes of force are applied to one or more device components, between the first and second magnitudes, based on one or more of: patient comfort, desired therapeutic effect, or patient wake or sleep state.

The present invention discloses methods and devices that are attached to regions of a patient's tongue. Interventions on certain areas of the tongue such as the tongue base have a high risk of causing heavy bleeding and also tongue swelling which may block the airway. This is especially a concern in certain patients with obstructive sleep apnea that have airways that can be blocked even with minor swelling of the tongue base. Further, the posterior regions of the tongue are sensitive and interventions there can trigger a strong gag reflex. Device embodiments, comprising small separable parts, that are placed in the mouth carry a risk of the small parts separating in the mouth and creating a choking hazard. The various embodiments described herein address these safety concerns. Several method and device embodiments describe minimally invasive or non-invasive interventions in tongue regions away from the tongue base. Further, the tongue remodels in response to long-term tongue implants. Such remodeling may reduce the long-term efficacy of implant-based procedures. The various embodiments described herein address these efficacy concerns.

In this specification, forces and alignments are often described in terms of directions. The convention used is shown in FIG. 1. FIG. 1 shows a section through a human head showing the general anatomy and the convention used to indicate direction, as used herein. Anterior direction is used to describe the direction towards the front of the patient, posterior direction is used to describe the direction towards the back of the patient, superior direction is used to describe the direction towards the top of the patient's head, and inferior direction is used to describe the direction towards the soles of the patient's feet.

Figure 3:
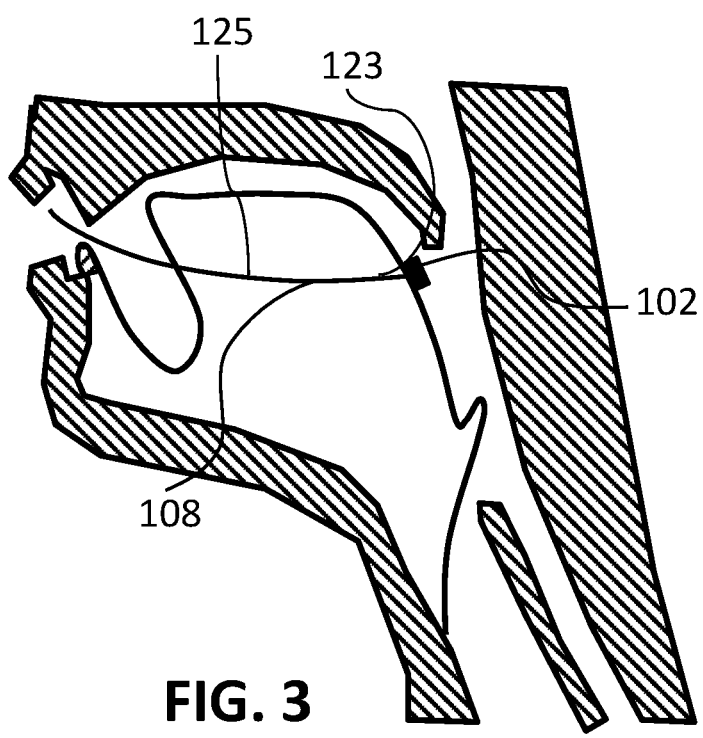
FIG. 3 shows one embodiment of a method of passing a tongue elongate member through a tongue and coupling a tongue anchor to the tongue elongate member on a dorsal surface of the tongue.
Figure 4:
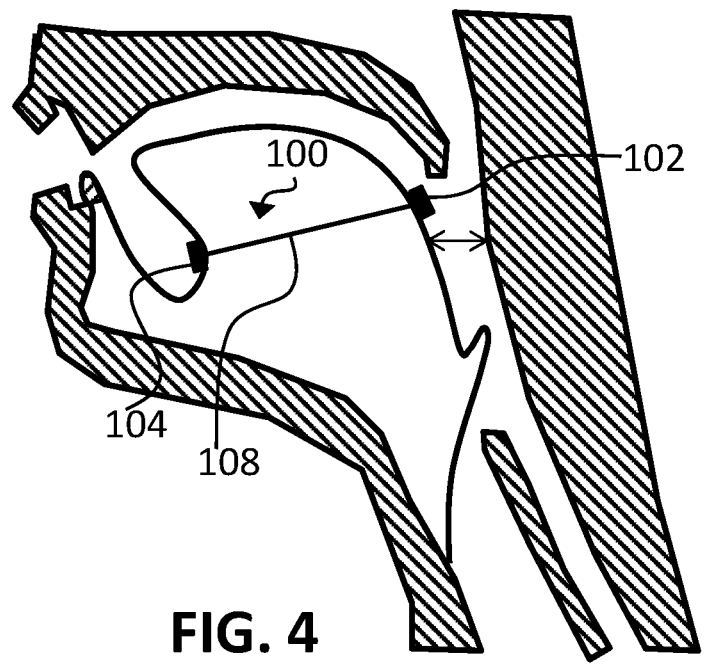
FIG. 4 shows one embodiment of a method of securing a second tongue anchor to an opposite end portion of the tongue elongate member.
Figure 5:
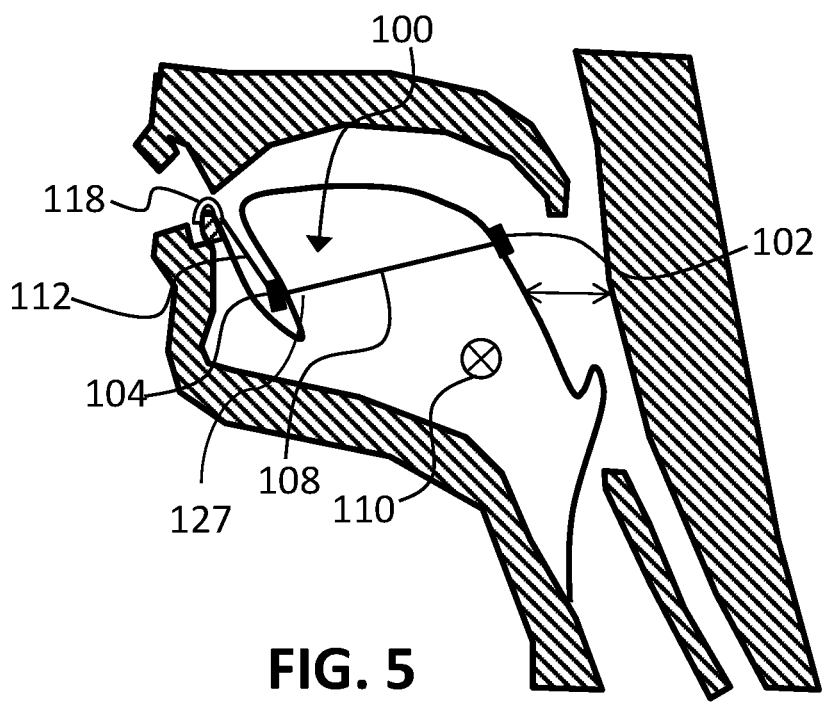
FIG. 5 shows one embodiment of a method of securing the elongate member to a bodily portion using an external anchor.

FIGS. 2-6 show a section through a human head showing the steps of an embodiment of a method of the present invention. At the step of FIG. 2, a penetrating element 120 is used to penetrate a portion of a patient's tongue. Examples of penetrating elements 120 include, but are not limited to needles, cannulas, stylets, trocars, and similar designs. Penetrating element 120 may comprise one or more hollow lumens. In the embodiment shown, a first end 121 of the penetrating element 120 pierces or penetrates a region on the ventral surface of the tongue, passes through a portion of the tongue, and emerges out of a region on the dorsal surface of the tongue. For example, the region of the tongue through which the penetrating element 120 exits may be a mid-region of the tongue, as opposed to a base or tip of the tongue. Further, as shown in FIG. 3, first tongue anchor 102 and first tongue elongate member 108 are placed in the anatomy using the penetration tract created by element 120. In one method embodiment, penetrating element 120 comprises a lumen and first elongate member 108 and anchor 102 are passed through the lumen of penetrating element 120. Once first elongate member 108 and anchor 102 are in place, penetrating element 120 is removed keeping first elongate member 108 and anchor 102 in the anatomy. First tongue anchor 102 may be placed on the dorsal surface of the tongue at a region defined by one or more anatomical landmarks. Examples of such landmarks include, but are not limited to: circumvallate papillae, distance from the tongue tip, distance from the lateral edges of the tongue, etc. In one such embodiment, first tongue anchor 102 is placed on the dorsal surface of the tongue at a region anterior to the circumvallate papillae. A first end 123 of elongate tongue member 108 is coupled to and extends from the first tongue anchor 102. A mid-portion 125 of the elongate tongue member 108 passes through a length of the tongue and emerges out of a region on the ventral surface of the tongue. The length of the tongue through which elongate tongue member 108 passes may range from about 1 cm to about 5 cm; about 0.5 cm to about 3 cm; about 2.5 cm to about 5 cm; about 3 cm to about 6 cm; etc. The region may be defined by one or more anatomical landmarks. Examples of such landmarks include, but are not limited to: tongue body, circumvallate papillae, distance from the tongue tip, distance from the lateral edges of the tongue, distance from the tongue base, etc. Further, as shown in FIG. 4, a second tongue anchor 104 is attached to a second end 127 of tongue elongate member 108. The attachment between the second tongue anchor 104 and the tongue elongate member 108 may be adjustable, reversible, or otherwise removable or adaptable. First tongue anchor 102 may be placed further posterior along the tongue than second tongue anchor 104, such that first tongue anchor 102 is positioned posteriorly and away from the teeth, and more superiorly than second tongue anchor 104. At this location, there is more space in the mouth for first tongue anchor 102. Further, as shown in FIG. 5, device 100 comprising first tongue anchor 102, first tongue elongate member 108, and second tongue anchor 104 is attached to an anatomical region. The attachment is through a second external elongate member 112 that attaches to an external anchor 118 that in turn attaches to a bodily region. In the embodiment shown, external anchor is a dental anchor and the bodily region is a region of the patient's teeth or gums.

Any of the dental anchors or other oral anchors disclosed herein may be designed such that they don't interfere with the natural closing (i.e., physiologic resting position) of the mouth. In one embodiment, the region of the anchor that lies between the patient's upper (maxillary) and lower (mandibular) teeth may be thin enough (e.g., having a thickness about less than 2 mm) such that the patients upper and lower teeth can close naturally when the patient is asleep. In such embodiments, a thickness of a dental anchor over an occluding surface of a tooth may be less than a thickness of the dental anchor over a non-occluding surface (e.g., a lateral surface) of the tooth. In one embodiment, a dental anchor is designed such that it fits into the freeway space i.e., the space between the occluding surfaces of the upper and lower teeth when the mandible is in physiologic resting position. Any of the anchors disclosed herein may be custom designed to fit the patient's anatomy. Such designs allow the patient to sleep more naturally when using the present invention.

Any of the dental anchors disclosed herein may be attached to one or more "side" teeth. Examples of side teeth include, but are not limited to: premolars and molars. In such embodiment, a component of the tension within an elongate member (e.g., elongate member 108, elongate member 112, etc.) is oriented to sideways or along the coronal plane. This force may deviate the tongue to one side when the patient is using the device embodiments of the present invention. Such embodiments are especially suited for patients who are side sleepers. The type and/or location of the dental anchor may be chosen based on which side the patient typically sleeps. In one such embodiment, a dental anchor is attached to a patient's left-side tooth if the patient sleeps on the right side. In one such embodiment, a dental anchor is attached to a patient's right-side tooth if the patient sleeps on the left side. In one embodiment, two dental anchors are attached: one on a left-side tooth and one on a right-side tooth such that the anchoring restricts tongue collapse on either side.

As used herein, external elongate member 112, 114 may form part of the same elongate member as tongue elongate member 108 or external elongate member 112, 114 may be separate from tongue elongate member 108. Said another way, any of the devices described herein may use one elongate member, two elongate members, three elongate members, etc. to accomplish the intended function of the device. Referring to the elongate members separately or as one elongate member is only intended to facilitate description of the various device configurations.

Embodiments of the present invention may be designed and/or placed to produce a clinical effect by a first mechanism discussed in this paragraph. For example, the devices described herein may only apply force to the tongue when the tongue falls back posteriorly. The attachment of device 100 to the region of the patient's teeth or gums may not produce a significant forward displacement force on the tongue when the patient is awake. However, when the patient sleeps, device 100 prevents or restricts the posterior region of the tongue from collapsing on to the posterior wall of the pharynx. In some embodiment herein, device 100 prevents or restricts the posterior movement of the body of the tongue. This is achieved through a therapeutic displacement force created by device 100, wherein at least one component of the displacement force is directed along the anterior direction, such that the displacement force prevents or reduces the posterior displacement of a portion of the posterior tongue when the patient sleeps. The displacement force may be generated using an anatomical region exterior to the tongue. At least one portion of the tongue may be prevented from being displaced in the posterior direction. At least one component of the displacement force is directed along the anterior direction, such that the displacement force causes displacement of a portion of the posterior tongue. In some embodiments herein, device 100 causes displacement of the body of the tongue. The displacement force may be generated using an anatomical region exterior to the tongue. The displacement force may be sufficient to overcome the effect of gravity on the tongue. At least one portion of the tongue is displaced in the anterior direction. As shown in FIG. 5, the displacement force has prevented one or more portions of the tongue from rotating about a rotation axis 110 in a clockwise direction. The rotation axis 110 is perpendicular to the plane of the figure (i.e., perpendicular to the mid-sagittal plane). The prevention or reduction of displacement of the tongue reduces the resistance to airflow in the patient's airway (e.g., in the oropharynx or hypopharynx) by portions of the tongue (e.g., portions of the tongue base). The displacement force may be zero when the patient is awake. For example, the connection between an external anchor (e.g., anchor 118 of FIG. 5) and a tongue anchor (e.g., anchor 104 of FIG. 5) may be removed or disconnected/ detached when the patient is awake. Any of the external anchors disclosed herein (e.g., anchor 118 of FIG. 5) may be removed when the patient is awake.

Embodiments of the present invention may be designed and/or placed to produce a clinical effect by a second mechanism discussed in this paragraph. Device 100 itself or the attachment of device 100 to an anchoring region (e.g., a region of the patient's teeth or gums) produces a therapeutic displacement force on the tongue. At least one component of the displacement force is directed along the anterior direction, such that the displacement force causes displacement of a portion of the posterior tongue such that the tongue is displaced more anteriorly than its physiological resting position. In some embodiments herein, device 100 causes displacement of the body of the tongue. The displacement force may be generated using an anatomical region exterior to the tongue. At least one portion of the tongue is displaced in the anterior direction. As shown in FIG. 1E, the displacement force has caused one or more portions of the tongue to rotate about a rotation axis 110 in a counter-clockwise direction. The rotation axis 110 is perpendicular to the plane of the figure. The displacement of the tongue reduces the resistance to airflow in the patient's airway (e.g. in the oropharynx or hypopharynx) by portions of the tongue (e.g. portions of the tongue base). The displacement force may be zero when the patient is awake. For example, the connection between an external anchor (e.g., anchor 118 of FIG. 5) and a tongue anchor (e.g., anchor 104 of FIG. 5) may be removed or disconnected/detached when the patient is awake. Any of the external anchors disclosed herein (e.g., anchor 118 of FIG. 5) may be removed when the patient is awake.

In any of the embodiments herein, the patient may adjust the displacement force or other parameters including, but not limited to: the placement or positioning of one or more device components (e.g., first tongue anchor, second tongue anchor, external anchors, etc.), the amount of displacement(s) (e.g., tension on a tongue elongate member, length of tongue elongate member, force exerted on the tongue by the tongue elongate member, force exerted on the tongue by the external elongate member, etc.), distance by which the tongue can move posteriorly before a therapeutic force starts to act, etc. The adjustment(s) may be done before the patient goes to sleep. In one embodiment, the patient starts the therapy with a lower therapeutic force or less tension on the tongue elongate member. The patient then adjusts one or more parameters of the device such that the force increases gradually over one or more days. The force may be increased until a desired therapeutic effect is obtained and/or the patient has trouble tolerating the device. The force and other parameters of the device embodiments herein may be adjusted multiple times by the patient. One of the key advantages of the embodiments disclosed herein is that the devices can be easily adjusted multiple times by the patient.

Embodiments disclosed herein may exert a displacement force ranging from about 0.01 N to about 5 N; about 0.2 N to about 3 N; about 1N to about 2N; about 0.05 N to about 2.5 N; about 1 N to about 5 N; etc. on one or more portions of the tongue and/or an anchor when the patient is sleeping. Embodiments disclosed herein may exert a displacement force such that the anterior component of the displacement force ranges from about 0.01 N to about 5 N on one or more portions of the tongue and/or an anchor when the patient is sleeping. Embodiments disclosed herein may produce a tension ranging from about 0.01 N to about 5 N within one or more regions of device 100 when the patient is sleeping. Examples of such regions include, but are not limited to one or more of: elongate members 108 and/or elongate members 112 and/or elongate members 114 disclosed herein.

Figure 6:
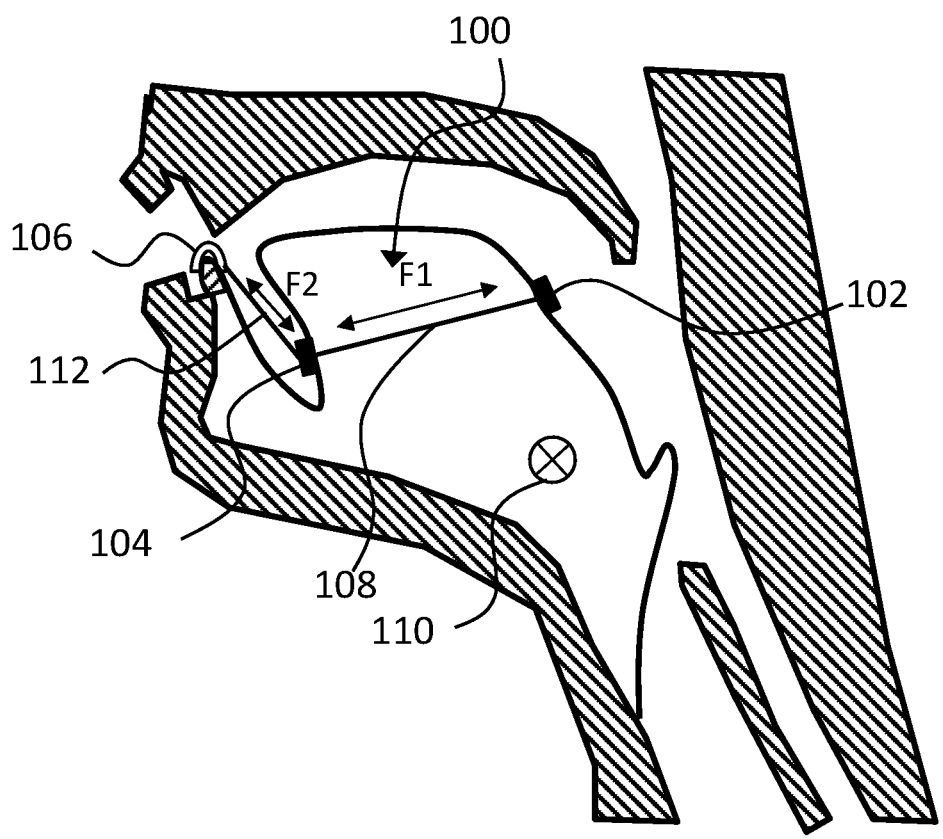
FIG. 6 shows one embodiment of a method of adjusting a displacement force on the tongue.

FIG. 6 shows the step of adjusting the displacement force on the tongue. Such a step of adjusting the displacement force may be used in any of the embodiments disclosed herein. Such adjusting of the displacement force may be performed by adjusting the tension in any of the elongate members disclosed herein. For example, as shown by arrow F1, a length of the tongue elongate member 108, or a length of tongue elongate member 108 between a first tongue anchor 102 and a second tongue anchor 104, may be increased or decreased to adjust displacement of the tongue. Further, for example, as shown by arrow F2, a length of external elongate member 112, or a length of the elongate member 112 that is between the second tongue anchor 104 and the external anchor 106, may be increased or decreased to adjust displacement of the tongue. The displacement force may be adjusted by methods including, but not limited to one or more of: changing the region of the patient's anatomy (e.g., teeth, gums, face, etc.) to which one or more portions (e.g., anchors) of device 100 attach, changing one or more physical parameters (e.g., length, stiffness, flexibility, elasticity, etc.) of any component (examples include, but are not limited to: anchors, elongate members), changing the location and/or orientation of any component (examples include, but are not limited to: anchors, elongate members), etc.

In some embodiments, adjusting the displacement force includes, but is not limited to: increasing or reducing a physiological effect of the invention, reducing a force on the tongue, increasing a force on the tongue, reducing a tension between the first and second tongue anchors, increasing a tension between the first and second tongue anchors, increasing an anterior displacement of the tongue, reducing an anterior displacement of the tongue, increasing a posterior displacement of the tongue, reducing a posterior displacement of the tongue, reducing one or more side-effects, reducing an abnormal sensation (e.g., pain/discomfort, excessive pulling sensation, excessive saliva production, etc.) felt by the patient, and producing a sensation (e.g., slight discomfort, pulling sensation, etc.) felt by the patient when the patient's tongue loses muscle tone. The step of adjusting the displacement force may be performed multiple times in the same patient. The step of adjusting the displacement force may be performed by a medical professional or by the patient.

In one such embodiment, the displacement force is increased to increase the displacement of the tongue in the anterior direction to increase the therapeutic effect of the invention. In another such embodiment, the displacement force is decreased to decrease the displacement of the tongue in the anterior direction to reduce the pain/discomfort felt by the patient.

Figure 7:
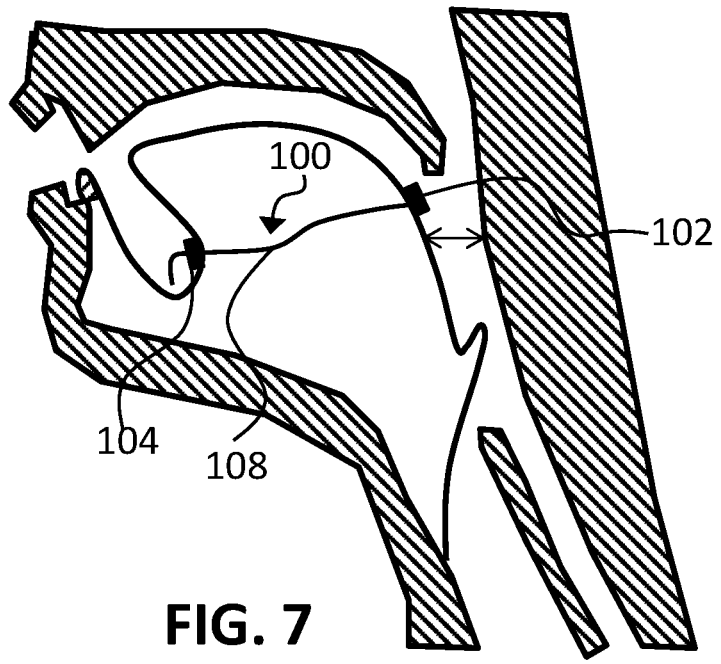
FIG. 7 shows one embodiment of an elongate member reversibly attached to a second tongue anchor.
Figure 8:
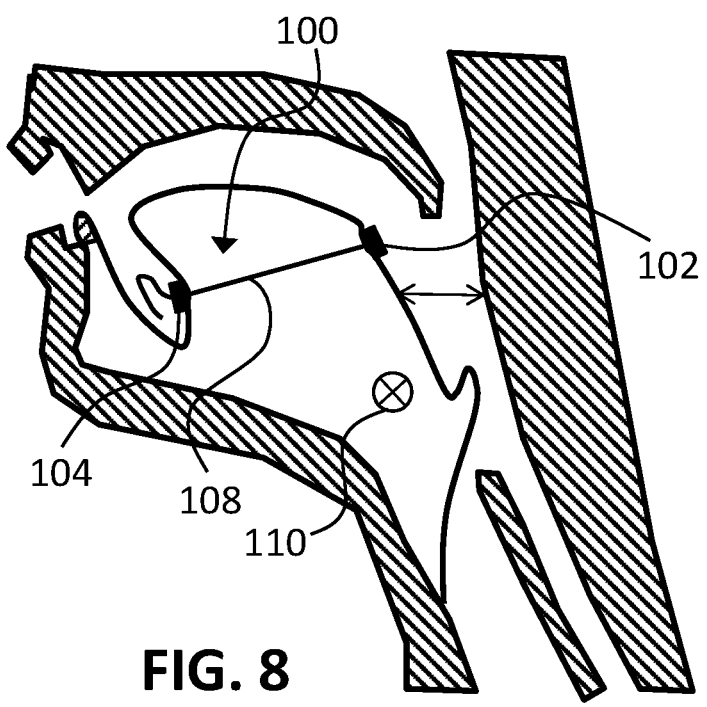
FIG. 8 shows one embodiment of an elongate member in a sliding arrangement relative to a second tongue anchor.

FIGS. 7-8 show a section through a human head showing an embodiment of the present invention comprising two anchors wherein the distance between the two anchors is adjusted to adjust the displacement force. In one such embodiment, as shown in FIG. 7, elongate member 108 is reversibly attached to second tongue anchor 104, such that second tongue anchor 104 can be attached and unattached from elongate member 108 to adjust a displacement force on the tongue. In another such embodiment, as shown in FIG. 8, tongue elongate member 108 is in a sliding arrangement relative to second anchor 104. For example, the second tongue anchor 104 may comprise a slide lock clasp, an adjustable slider clasp, a toggle spring stop, magnetic clasp, barrel clasp, clasp closure, clamp, spring coil, etc. Such adjustable designs may also be used for other embodiments disclosed herein including, but not limited to the embodiments shown in FIGS. 50-51.

Figure 9:
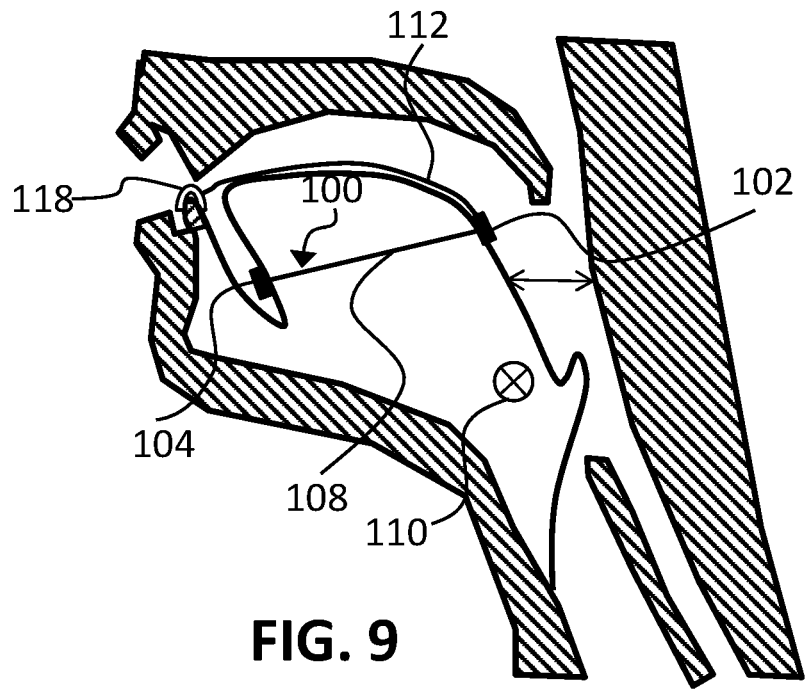
FIG. 9 shows one embodiment of an external elongate member reversibly attached or in sliding arrangement relative to a first tongue anchor.

In some embodiments, as shown in FIG. 9, an external or dorsal elongate member 112, coupled to external anchor 118, extends from the first tongue anchor 102, as opposed to the second tongue anchor 104. Tongue elongate member 108 extends between first tongue anchor 102 and second tongue anchor 104, but in this embodiment, the first tongue anchor 102 is either reversibly attached or slidably attached to tongue elongate member 108, as described above in FIGS. 7-8 for second tongue anchor 104.

Figure 10:
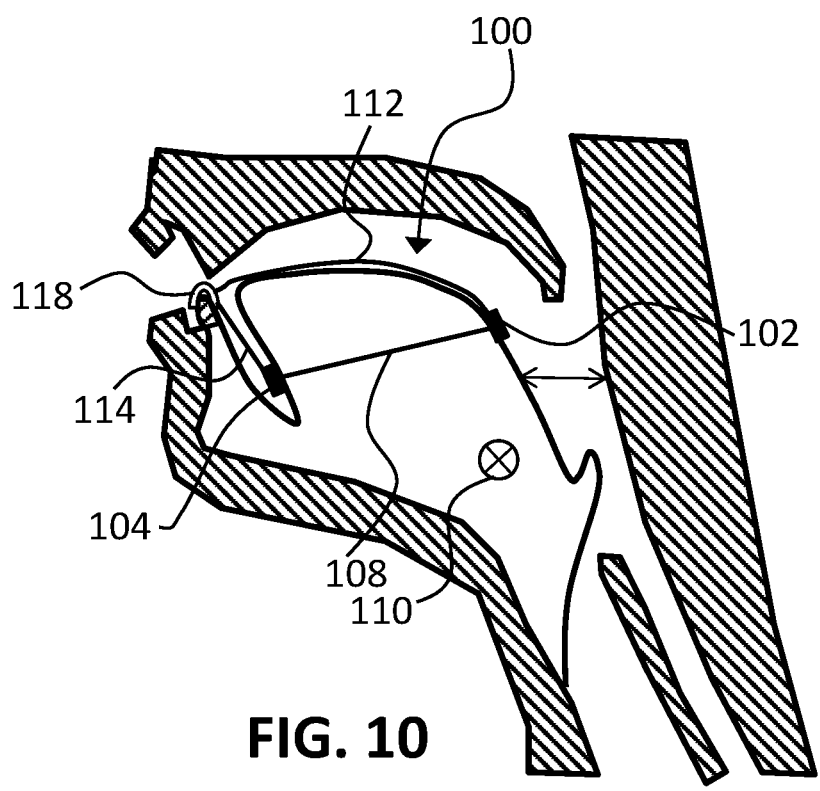
FIG. 10 shows one embodiment of an external elongate member extending from a second tongue anchor and a dorsal elongate member extending from a first tongue anchor, both of which are attached to an external anchor.

Further, as shown in FIG. 10, both a first tongue anchor 102 and a second tongue anchor 104 may interact with an external anchor 118. In such an embodiment, a dorsal elongate member 112 extends from the first tongue anchor 102 and a ventral or external elongate member 114 extends from the second tongue anchor 104. shows a section through a human head showing an embodiment of the present invention comprising a first tongue anchor, a second tongue anchor, and an external anchor. In this embodiment, external anchor 118 anchors to a region on the teeth of the patient. In this embodiment, second anchor 104 is connected to external anchor 118 through a third elongate member 114.

Figure 11:
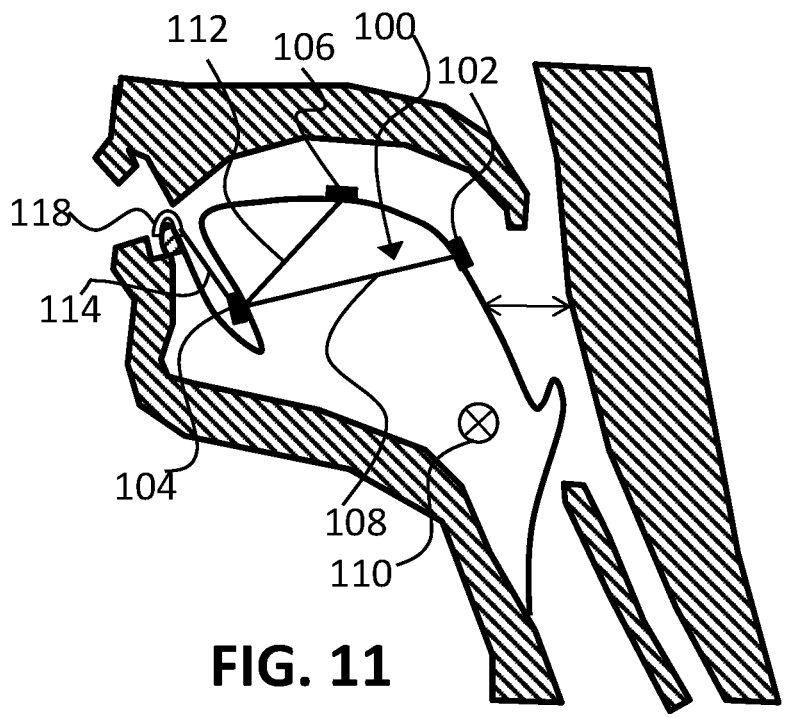
FIG. 11 shows one embodiment of a device comprising two substantially dorsally positioned tongue anchors and one substantially ventrally positioned tongue anchor.

In still another embodiment, as shown in FIG. 11, a first tongue anchor 102 is positioned substantially dorsally on the tongue and a second tongue anchor 104 is positioned substantially ventrally on the tongue, as shown elsewhere herein; however, in this embodiment, a third tongue anchor 106 is also positioned substantially dorsally on the tongue, but more anteriorly than first tongue anchor 102. As such, the tongue is engaged at three points 102, 104, and 106 and a displacement force is applied along a lower elongate member 108 and an upper elongate member 112, each of which extend through at least a portion of the tongue. Further one or both elongate members 108, 112 may be adjustable through, via, or at second or ventral tongue anchor 104. External elongate member 114 extends from second tongue anchor 104 and engages with external anchor 118.

Figure 12:
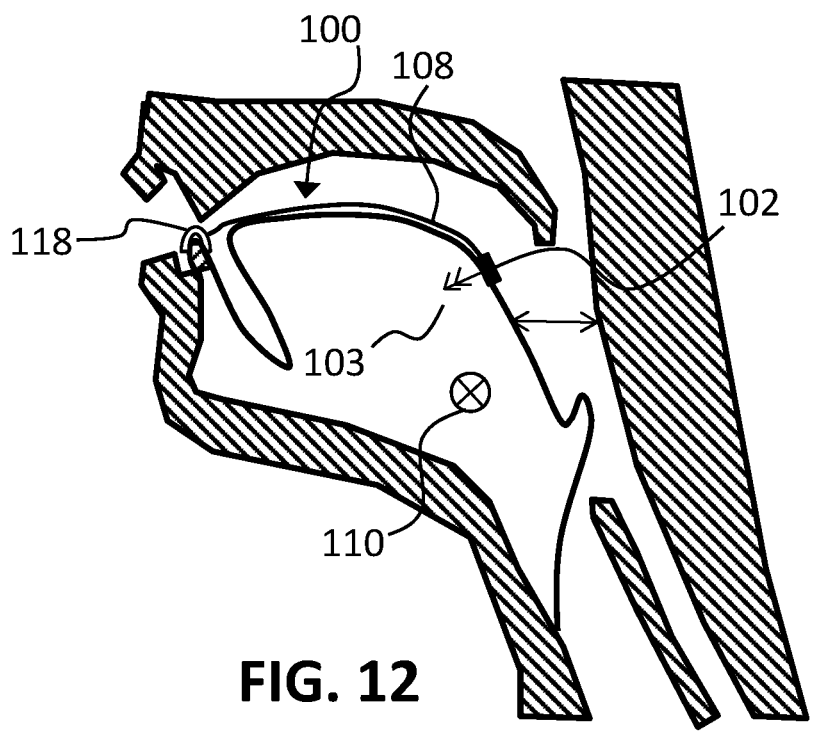
FIG. 12 shows one embodiment of a device comprising a first or dorsal tongue anchor comprising one or more tissue penetrating elements.

FIG. 12 shows a section through a human head showing an embodiment of the present invention comprising a dorsal tongue anchor and an external anchor wherein at least one portion of the dorsal tongue anchor is embedded into the tongue. Dorsal tongue anchor 102 comprises one or more tissue penetrating elements regions 103, examples of which include, but are not limited to: sharp tips, barbs, bent or curved regions, hooks, etc. The one or more tissue penetrating elements or regions 103 penetrate the tongue and anchor dorsal tongue anchor 102 to a region of the tongue, for example a dorsal region of the tongue.

Figure 13:
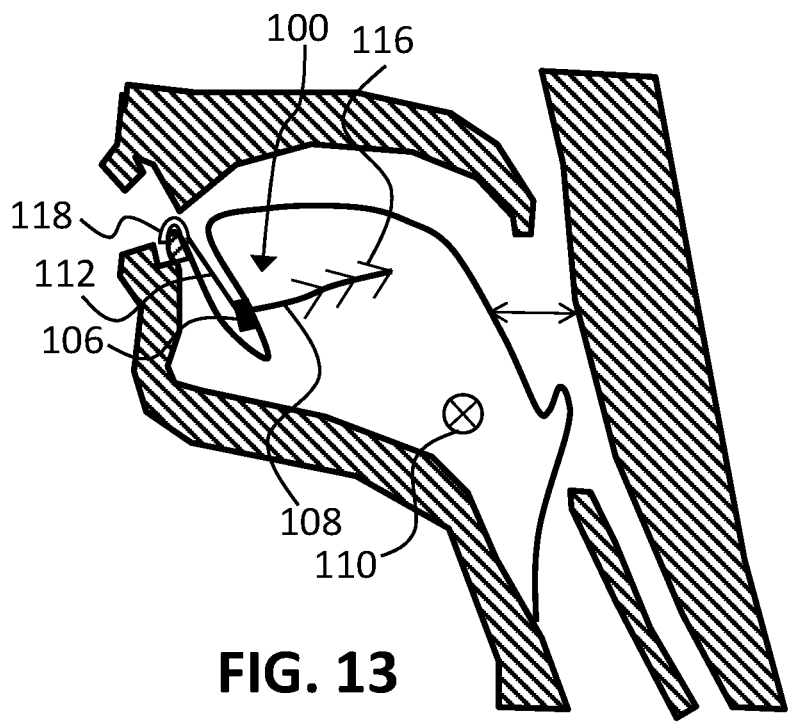
FIG. 13 shows one embodiment of a device comprising a second or ventral tongue anchor comprising one or more tissue penetrating elements.

FIG. 13 shows a section through a human head showing an embodiment of the present invention comprising a ventral tongue anchor 106 with one or more tissue penetrating elements 116 and an external anchor 118. Ventral anchor 106 is coupled to external anchor 118 via external elongate member 112, as described elsewhere herein. Ventral anchor 106 includes one or more tissue penetrating elements 116, examples of which include, but are not limited to: sharp tips, barbs, bent or curved regions, hooks, etc. The one or more tissue penetrating elements 116 embed into the tongue and anchor ventral anchor 106 to a region of the tongue, for example a ventral region of the tongue.

Figure 14:
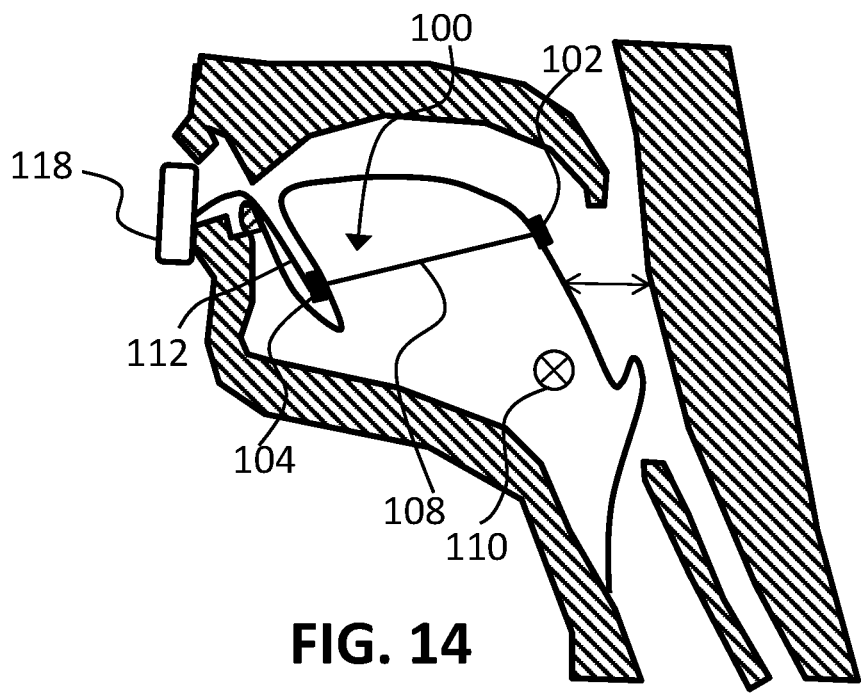
FIG. 14 shows one embodiment of a device comprising an external anchor that attaches to an external fixture.

FIG. 14 shows a section through a human head showing an embodiment of the present invention comprising a first or dorsal tongue anchor, a second or ventral tongue anchor, and an external anchor located outside the mouth of the patient. As shown in FIG. 14, examples of external anchor 118 include, but are not limited to: headgear; facemasks; attachments attached to the patient's head using mechanisms such as straps, adhesives, clips, bands, hooks, etc.; harnesses; head straps; and caps. In one such embodiment, external anchor 118 is similar to an anesthesia mask harness that is attached to the patient's head using one or more flexible and/or elastic straps. Further, as described elsewhere herein, tongue elongate member 108 connects first tongue anchor 102 to second tongue anchor 104 and second tongue anchor is connected to external anchor via external elongate member 112.

Figure 15:
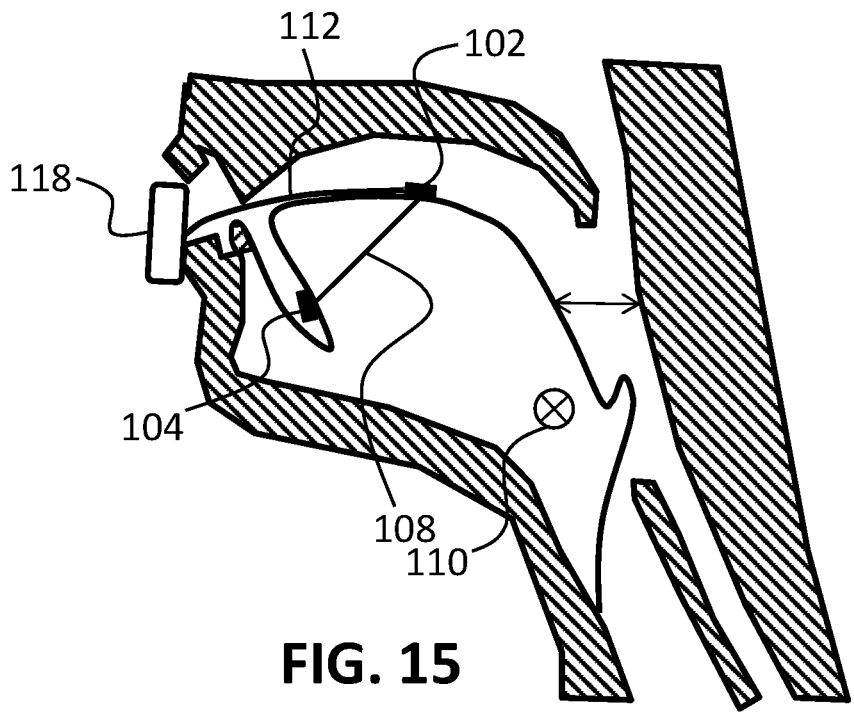
FIG. 15 shows another embodiment of a device comprising an external anchor that attaches to an external fixture.

FIG. 15 shows a section through a human head showing another embodiment of the present invention comprising a first or dorsal tongue anchor 102, a second or ventral tongue anchor 104, and an external anchor located outside the mouth of the patient, similar to that already described with respect to FIG. 14. In this embodiment, dorsal tongue anchor 102 is coupled to external anchor 118 via dorsal or external elongate member 112, as shown and described in FIG. 9.

Figure 16:
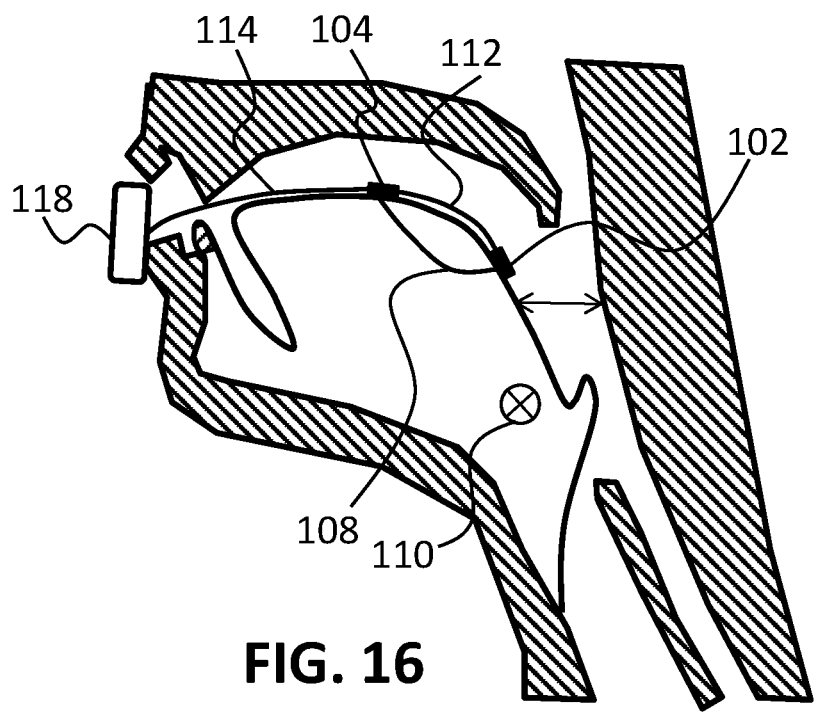
FIG. 16 shows another embodiment of a device comprising an external anchor that attaches to an external fixture.

FIG. 16 shows a section through a human head showing another embodiment of the present invention comprising a first dorsal tongue anchor 102, a second dorsal tongue anchor 104, and an external anchor 118 located outside the mouth of the patient, as described in FIG. 14. First dorsal tongue anchor 102 is positioned more posteriorly than second dorsal tongue anchor 104 or, said another way, second dorsal tongue anchor 104 is positioned more anteriorly than first dorsal tongue anchor 102. First elongate member 112 couples the first 102 and second 104 anchors and elongate member 114 couples the second tongue anchor to external anchor 118. As described elsewhere herein, first and second elongate members 112, 114 form a single elongate member that passes through or interacts with each anchor or they may be separate elongate members.

Figure 17A:
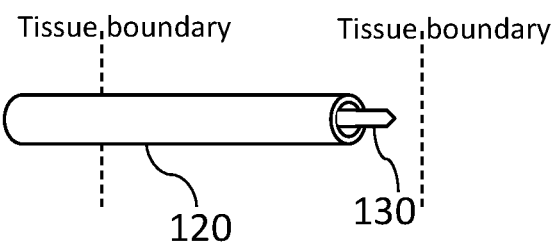
FIGS. 17A-17F show various steps of a method of positioning an elongate member through a tissue.
Figure 17B:
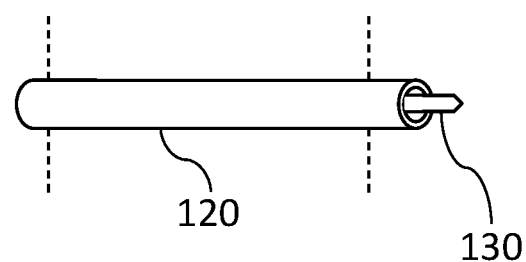
Figure 17C:
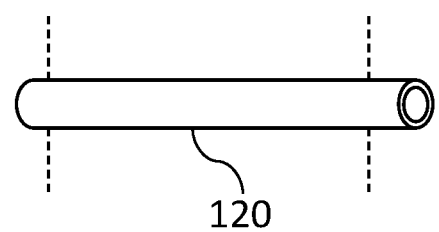
Figure 17D:
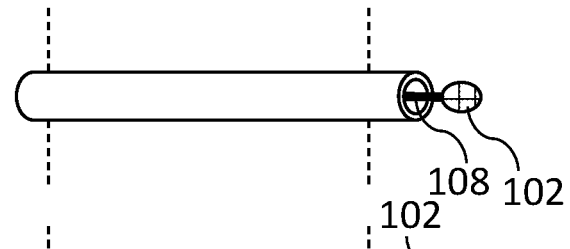
Figure 17E:
Figure 17F:
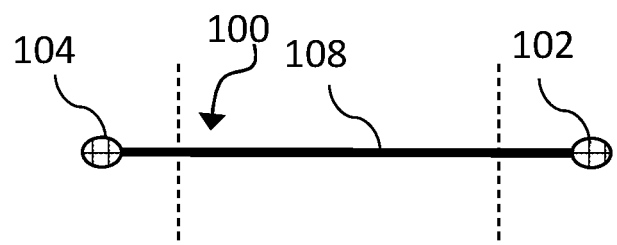

FIGS. 17A-17F show one embodiment of a method of placing device 100 across tissue. In FIG. 17A, a combination of penetrating element 120 and stylet 130 is used to pierce a tissue boundary. For example, a tissue boundary may include a surface of a tongue, a dorsal surface of a tongue, a ventral surface of a tongue, or other portion of a tongue. In other embodiments, tissue boundary may include a surface of an organ that needs to be retracted, for example to move it or displace it from a surgical field. In FIG. 17B, the combination of penetrating element 120 and stylet 130 is advanced such that the distal tip of penetrating element 120 emerges out of the tissue through another tissue boundary. In FIG. 17C, stylet 130 is removed without removing penetrating element 120. In FIG. 17D, first anchor 102 connected to an elongate member 108 is advanced through a lumen defined by penetrating element 120. In FIG. 17E, penetrating element 120 is removed leaving behind first anchor 102 connected to elongate member 108. In FIG. 17F, second anchor 104 is connected to elongate member 108 creating device 100. Although the above steps are described sequentially according to the figures, one of skill in the art will appreciate that the steps may be executed in any sequence without departing from the original scope or intent of this disclosure.

In this embodiment, a combination of penetrating element 120 and stylet 130 are used together to penetrate tissue. In other embodiments, penetrating elements, including, but are not limited to: laser emitting elements, mechanical members with a sharp tip, radiofrequency or microwave emitting elements, heating elements, elements loaded using a spring or other mechanical component, and a part of device 100, are used to penetrate one or more tissue regions.

Figure 18:
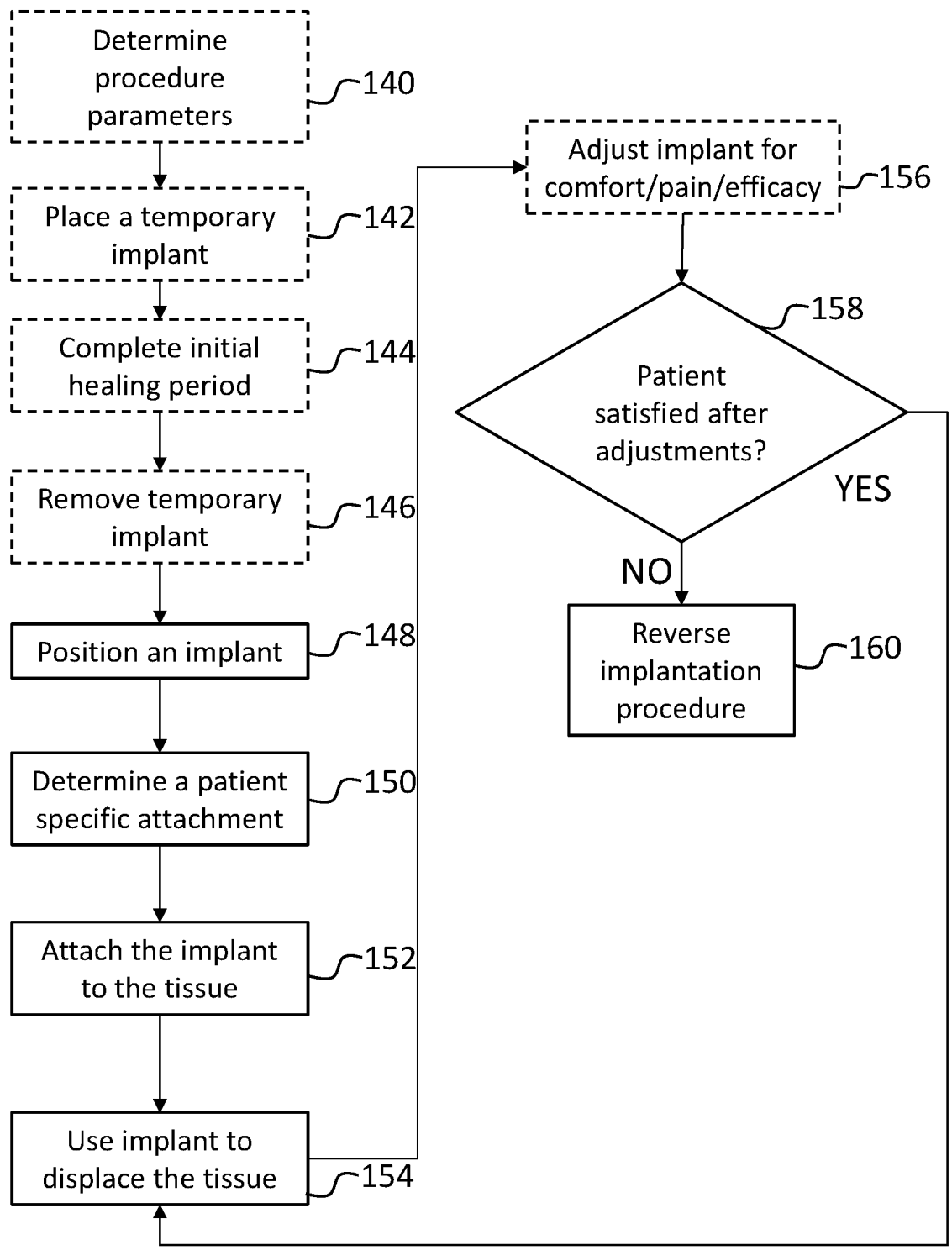
FIG. 18 shows one embodiment of a method of positioning or implanting a device.

FIG. 18 shows an embodiment of a method of the present invention wherein device 100 comprises a long-term (e.g., permanent, placed for more than a week, etc.) implant. At optional step 140, a healthcare provider (e.g., a surgeon, a dentist, physician, etc.) determines one or more parameters of the procedure. Examples of such parameters include, but are not limited to: type (including size) or number of components of device 100, location of placement of one or more implants, direction of one or more implants, degree of restriction and/or displacement of the tissue, direction and/or magnitude of forces to be applied to the tongue, etc. At optional step 142, a temporary implant is placed into the tissue. In one embodiment, the temporary implant is placed using one or more steps shown in FIGS. 17A-17F. At optional step 144, an initial healing period is completed. The healing period may range from 2-3 days to about a month. During the healing period, one or more of: swelling, inflammation, and pain may reduce. At optional step 146, the temporary implant is removed. At step 148, an implant (e.g., a long-term implant but could also be a short-term implant) is positioned in or relative to a tissue of the patient. Examples of such implants includes any of the implants disclosed elsewhere herein. At step 150, a patient specific attachment (e.g., an external anchor 118) is determined (e.g., a face mask, a dental attachment, gum attachment, a retainer attachment, a mouth guard attachment, etc.). Alternatively, a desired attachment may be selected for the patient. At step 152, attach the implant to the determined structure (e.g., face mask, teeth, gums, retainer, etc.). The device functions or is used to displace the tissue, as disclosed elsewhere herein. At optional step 156, the effect of the device is adjusted for one or more of: comfort/pain, pulling sensation, side effects, and/or efficacy. At step 158, a determination is made if the patient is satisfied with the implant and/or is obtaining the desired clinical effect. When the patient is satisfied, the patient continues to use the device and the method returns to step 154. When the patient is not satisfied at step 158, the implantation procedure is reversed at step 160. A major advantage of the minimally invasive methods and devices disclosed herein is that the entire clinical procedure can be reversed without causing long term or permanent changes to the patient's anatomy. Although the above steps are described sequentially according to the figures, one of skill in the art will appreciate that the steps may be executed in any sequence without departing from the original scope or intent of this disclosure.

Figure 19:
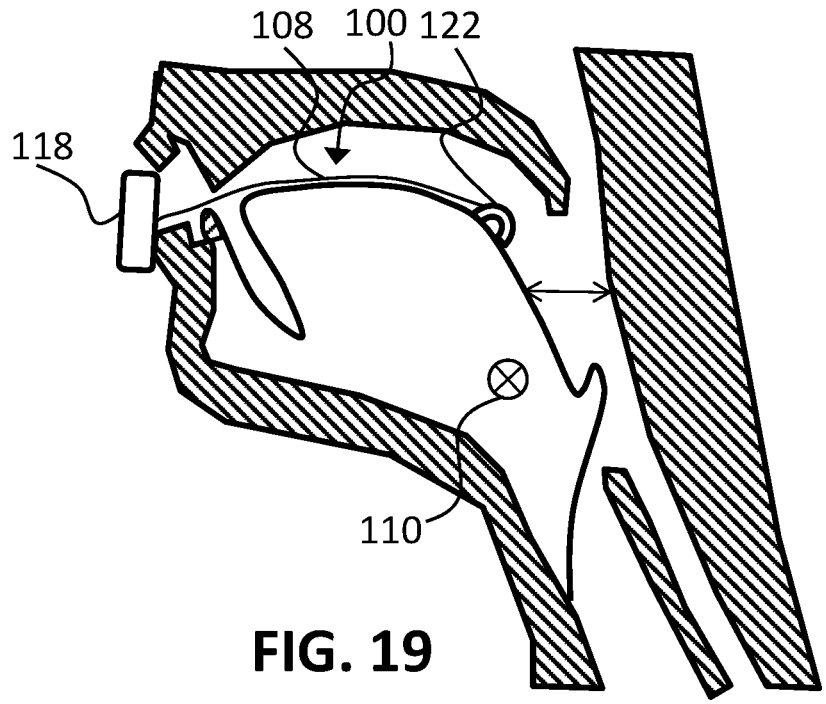
FIG. 19 shows one embodiment of a device comprising a surface anchor.

FIG. 19 shows a section through a human head showing an embodiment of the invention comprising a tongue surface anchor and an external anchor. In one method embodiment, temporary placement of devices 100 (e.g., those comprising a tissue surface anchor) is used to determine one or more of: patient tolerability to devices 100; resolution of symptoms; dimensions and/or type of one or more elements (e.g., anchors, elongate members, etc.) of devices 100; anatomical location and number of one or more implants, etc. This information, in turn, may be used to: decide the suitability of patients to more invasive devices 100 (e.g., those that involve tissue penetration); decide the aspects of subsequent procedures, e.g., placement of one or more anchors, type of anchors and elongate members, etc.

In one embodiment, surface anchor 122 is a suction anchor. Examples of suction anchors 122 include, but are not limited to: suction anchors 122 that are directly attached to a vacuum generating element; suction anchors 122 that are indirectly attached to a vacuum generating element; and suction anchors that have an integrated vacuum generating element. A suction anchor 122 may be attached to the vacuum generating element through one or more of: tethers, wires, tubes, pistons, elements comprising a displaceable portion that generates a vacuum, etc. Examples of vacuum generating elements include, but are not limited to: balloon structures, bulbs, vacuum and other pumps, syringes, elements comprising a displaceable portion that generates a vacuum, etc. In another embodiment, surface anchor 122 is an anchor attachable to a region of the tongue using glue. One or more portions of suction anchors may be made of rigid materials, examples of which include, but are not limited to: metals, plastics, polymers (e.g., silicone), rigid rubber materials, etc. One or more portions of suction anchors may be made of flexible materials, examples of which include, but are not limited to: metals, plastics, polymers (e.g., silicone), rubber materials, foams, gels, elastic materials, etc. To effectively maintain vacuum, one or more flexible materials such as foams and hydrocolloids may be used. Such materials may be a part of surface anchor 122 or a separate element. As shown and described elsewhere herein, surface anchor 122 may be coupled to elongate member 108, which is coupled to external anchor 118, for example anchored to a bodily portion (e.g., teeth, gums, etc.) or to a fixture (e.g., retainer, head gear, mask, etc.).

Any of the elongate members disclosed herein may be made of an elastic material. In such embodiments, the elastic elongate member(s) perform one or more actions including, but not limited to: allowing easier use of device 100, preventing excessive forces on that anatomy, maintaining a force on the anatomy, etc.

Figure 20:
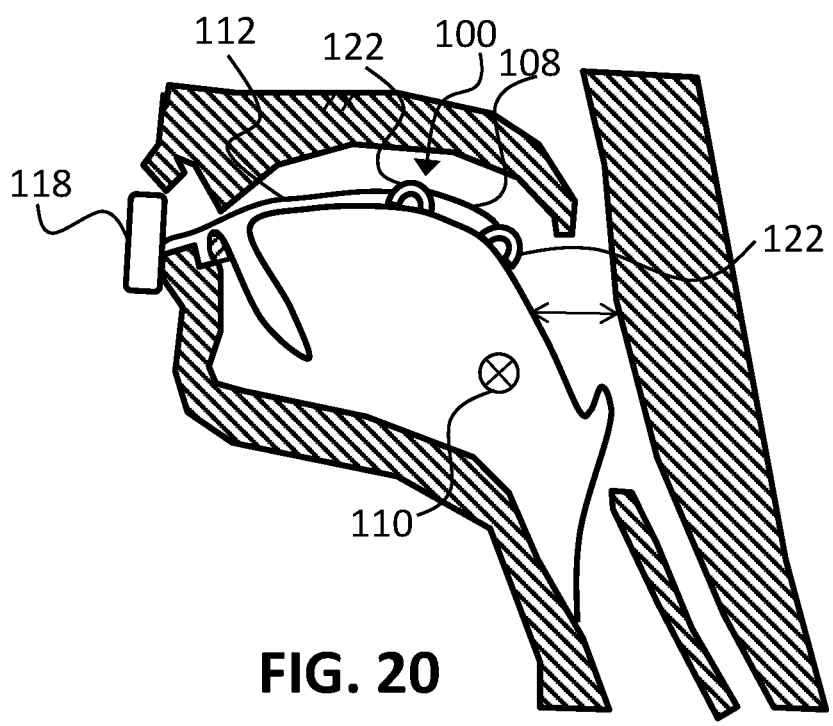
FIG. 20 shows another embodiment of a device comprising a surface anchor.

FIG. 20 shows a section through a human head showing an embodiment of the invention comprising two surface anchors (e.g., suction anchors) and an external anchor. In such an embodiment, a second surface anchor 122 may be positioned on the tissue more anteriorly than a first surface anchor 108. Said another way, a first surface anchor 108 may be positioned more posteriorly than a second surface anchor 122. Second surface anchor 122 may be coupled to an elongate member 122, which is coupled to external anchor 118, as described elsewhere herein.

Figure 21:
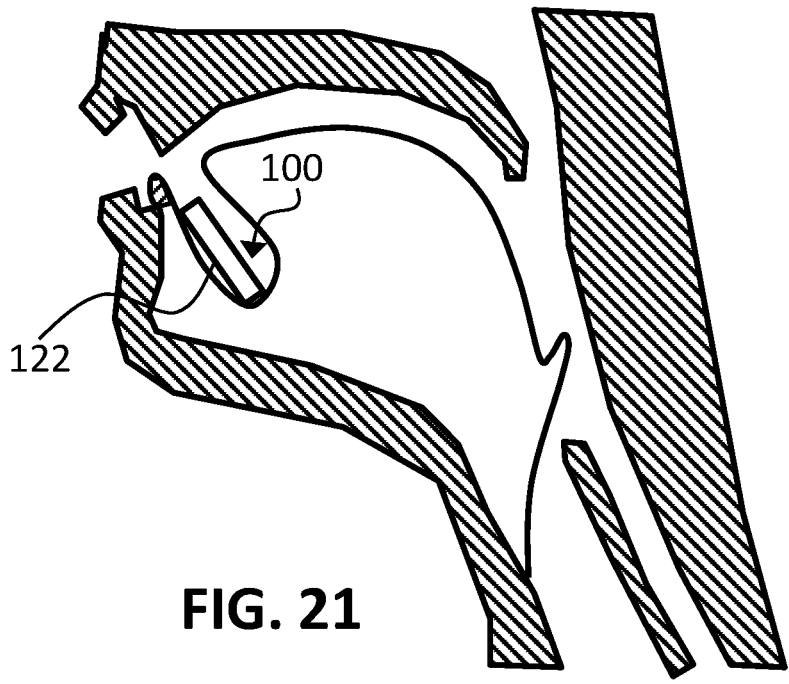
FIG. 21 shows another embodiment of a device comprising a surface anchor in an inactive configuration.
Figure 22:
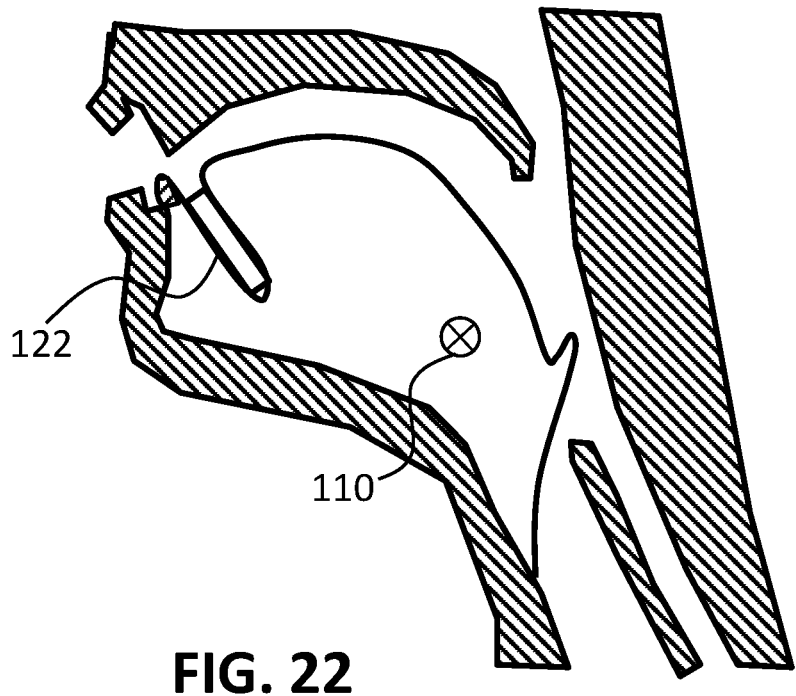
FIG. 22 shows another embodiment of a device comprising a surface anchor in an active configuration.

FIGS. 21-22 show a section through a human head showing an embodiment of a method of the present invention that uses a sub-lingual surface anchor 122 (e.g., a suction anchor). As shown in FIG. 21, a surface anchor 122 is positioned sub-lingually, between a floor of the mouth and a ventral surface of the tongue. FIG. 21 shows the inactive, no suction applied, configuration. In FIG. 22, suction is applied, creating an active configuration, to the surface anchor causing the tongue to move forward and contact the surface anchor 122.

Figure 23:
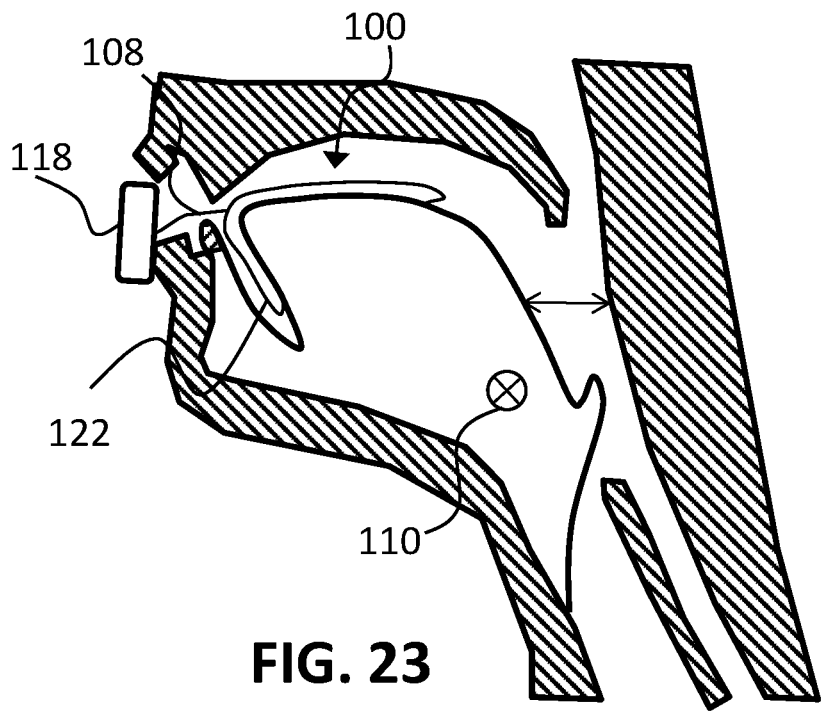
FIG. 23 shows another embodiment of a device comprising a surface anchor.

FIG. 23 shows a section through a human head showing another embodiment of the invention comprising a surface anchor 122 (e.g., a suction anchor) and an external anchor 118. In this embodiment, the surface anchor 122 is attached to the tip of the tongue. As shown in FIG. 23, surface anchor 122 contacts and interacts with at least a ventral portion of the tongue and at least a dorsal portion of the tongue. When vacuum is applied to surface anchor 122, surface anchor 122 securely holds the tongue and the tongue is displaced relative to the posterior wall of the pharynx by external anchor 118 that is coupled to surface anchor 122. External anchor 118 may couple to surface anchor at a tip of the tongue, on a ventral surface of the tongue, or on a dorsal surface of the tongue.

Figure 24:
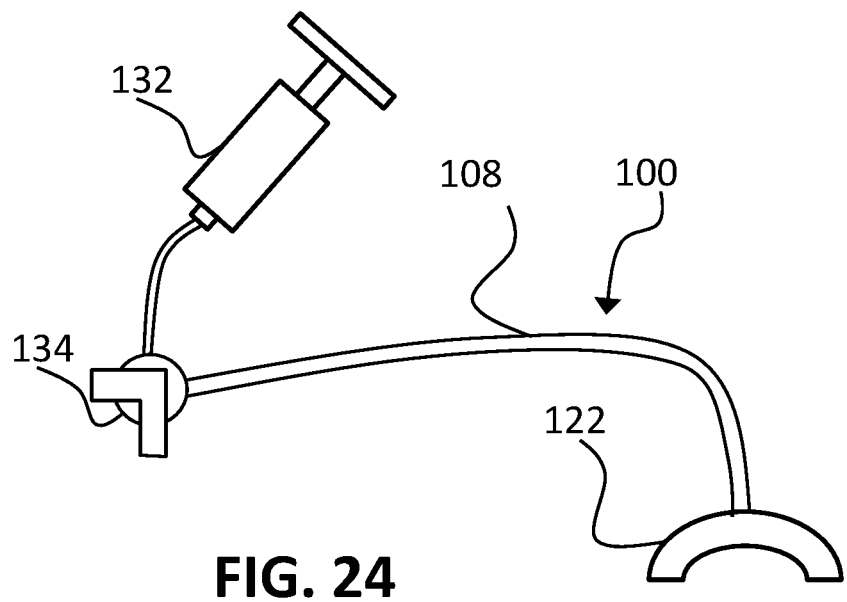
FIG. 24 shows another embodiment of a device comprising a surface anchor.

FIG. 24 shows a device embodiment of the present invention comprising a suction anchor than can be reversibly attached to a tongue. In FIG. 24, suction anchor 122 is connected to a syringe 132 through a first elongate member 108. First elongate member 108 is in fluid communication with syringe 132. For example, elongate member 108 may define a lumen therethrough that is in fluid communication with a chamber defined by syringe 132. Syringe 132 acts as a vacuum generating element. This embodiment further comprises a valve 134 (e.g., a stopcock, a self-sealing valve, etc.) that can be used to allow or block a fluid communication between syringe 132 and suction anchor 122. A user can keep valve 134 open and create a vacuum using syringe 132. Thereafter, the user can close valve 134 and remove syringe 132. In embodiments of self-sealing valves, the valve may be designed such that it opens when connected to a specific device (e.g., a syringe) and seals itself when the device is removed. The length and other dimensions of elongate member 108 may be such that suction anchor 122 is allowed to extend the tissue to a target displaced position while preventing the tongue from falling too deep into the patient's throat and obstructing the airflow.

Figure 25A:
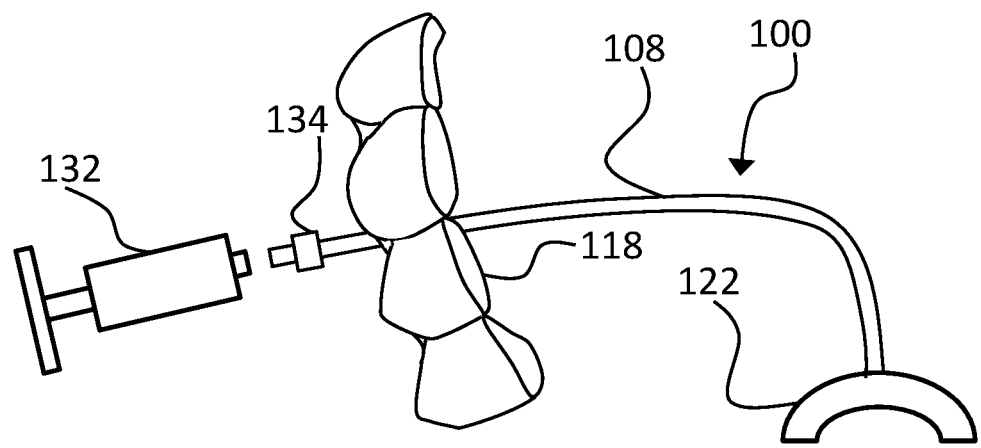
FIG. 25A shows another embodiment of a device comprising a surface anchor.

FIG. 25A shows an integrated device embodiment of the present invention wherein two anchors are connected to each other through an elongate member. In the embodiment shown, one of the anchors is a suction anchor 12 than can be reversibly attached to a tongue. Suction anchor 122 is connected to an external anchor 118 through a first elongate member 108. In one embodiment, suction anchor 122 is permanently connected to an external anchor 118 through a first elongate member 108. In another embodiment, suction anchor 122 is reversibly connected to an external anchor 118 through a first elongate member 108. The length of first elongate member 108 between suction anchor 122 and external anchor 118 may be adjustable. In method embodiments using such a design, the length of first elongate member 108 between suction anchor 122 and external anchor 118 may be adjusted based on parameters disclosed elsewhere in this specification. In the embodiment shown in FIG. 25, external anchor 118 is a dental anchor. One embodiment of vacuum generation is shown in FIG. 25. Vacuum is generated using a syringe 132 that is in fluid communication with suction anchor 122. A valve 134 (e.g., a stopcock, a self-sealing valve, etc.) may be provided that allows or blocks a fluid communication between syringe 132 and suction anchor 122. Valve 134 may be opened or kept closed to create/remove or maintain a vacuum. Valve 134 may be a self-sealing valve that opens when connected to a specific device (e.g., a syringe) and seals itself when the device is removed. The length and other dimensions of elongate member 108 may be such that suction anchor 122 is allowed to extend the tissue to a target displaced position while preventing the tongue from falling too deep into the patient's throat and obstructing the airflow.

Figure 25B:
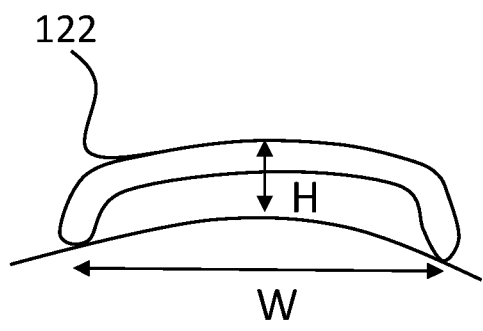
FIG. 25B shows a first configuration of an embodiment of a suction anchor.
Figure 25C:
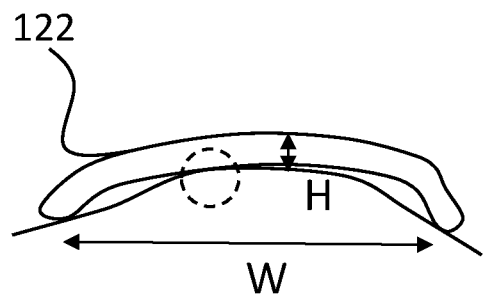
FIG. 25C shows a second configuration of the embodiment of FIG. 25B.

FIGS. 25B and 25C show two configurations of an embodiment of a suction anchor comprising a soft or deformable region. Any of the suction anchors 122 disclosed herein may comprise one or more regions that are soft enough to deform on application of a vacuum. For example, a tissue contacting region of suction anchor 122 may be made of a material that has a Shore A hardness of about less than 60 or a Shore 00 hardness of about less than 90. In a particular embodiment, a tissue contacting region of suction anchor 122 is made of a material that has a Shore A hardness of about less than 20 or a Shore 00 hardness of about less than 70. In a particular embodiment, a tissue contacting region of suction anchor 122 is made of a material that has a Shore 00 hardness of about less than 60. The non-tissue contacting regions of any suction anchors 122 disclosed herein may be made of harder or stiffer materials. Examples of materials that may be used to manufacture suction anchors 122 disclosed herein are mentioned elsewhere in this specification. FIG. 25A shows the shape of a soft suction anchor 122 before applying a vacuum. On applying a vacuum, the shape of suction anchor 122 changes as shown in FIG. 25B. As shown, the height H of suction anchor 122 reduces on application of a vacuum. Further, the width W of suction anchor 122 increases on application of a vacuum. Thus, on application of a vacuum, suction anchor 122 deforms and mechanically adjusts to the tongue surface instead of the tongue alone deforming into a shape that fits into a suction anchor 122. This design increases the comfort of the patient when using device 100 and also allows a better retention of a vacuum during use. For example, a height H between a first conformation (FIG. 25B) and a second conformation (FIG. 25C) may decrease by about 0.5×; about 1×; about 2×; about 3×; about 4×; between about 0.5× to about 2×; about 1× to about 3×; etc. Further for example, a width W between a first conformation (FIG. 25B) and a second conformation (FIG. 25C) may increase by about 0.5×; about 1×; about 2×; about 3×; about 4×; between about 0.5× to about 2×; about 1× to about 3×; etc.

Any of the anchors disclosed herein (including, but not limited to anchor 102 and anchor 104) may be manufactured using soft materials that deform during use. For example, anchor 102 and/or anchor 104 of FIG. 5 may deform when a force is applied in the step shown in FIG. 5. Such soft anchors are especially useful to increase the comfort of the patient e.g., during sleep. Further, soft anchors may be used to divide a force over a large tissue area, essentially reducing the pressure on a tissue area, which in turn helps to prevent and/or reduce one or more of: pain/discomfort, sensation of a foreign object, tissue necrosis, reduction in tissue perfusion, tissue erosion, and/or migration of device 100 components.

Any of the suction anchors 122 disclosed herein may be designed and used with a vacuum sufficient to distort tongue tissue and/or suction anchor 122 such that a portion of tongue tissue comes into physical contact with an inner portion of suction anchor 122. One example is shown in FIG. 25C, wherein the region where a portion of tongue tissue comes into physical contact with an inner portion of suction anchor 122 is marked with a dashed circle. Any of the suction anchors 122 disclosed herein may be designed such that the tissue contacting region of the suction anchor 122 is roughly planar such that the plane of the tissue contacting region is parallel to the plane of the contacted tissue. Any of the suction anchors 122 disclosed herein may be designed such that the region of contact between the suction anchor 122 and the tissue increases as the amount of applied vacuum increases. Such a design allows a better retention of a vacuum during use.

Figure 26:
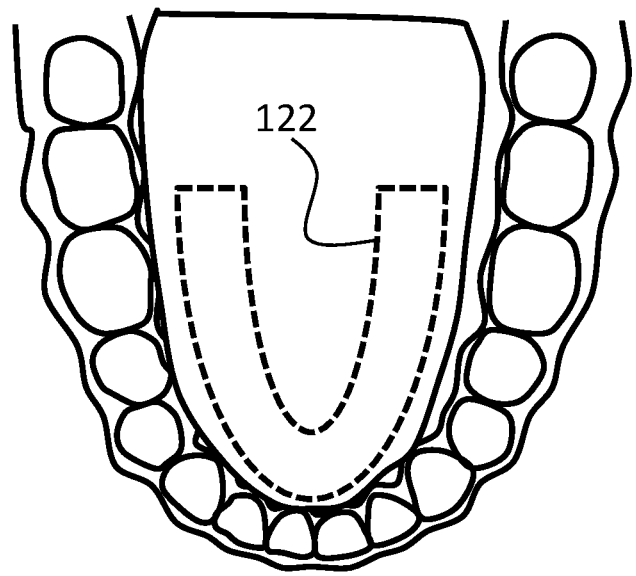
FIG. 26 shows one embodiment of a device comprising a sub-lingual anchor.
Figure 27:
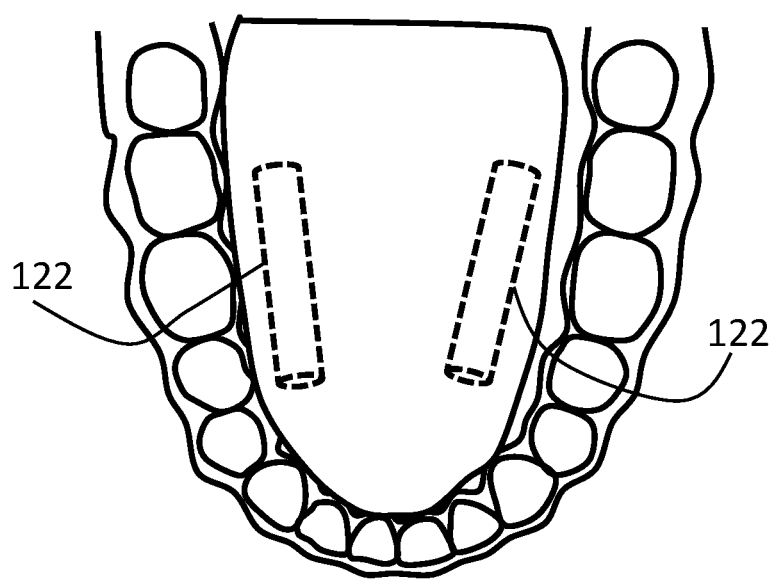
FIG. 27 shows another embodiment of a device comprising a sub-lingual anchor.
Figure 28:
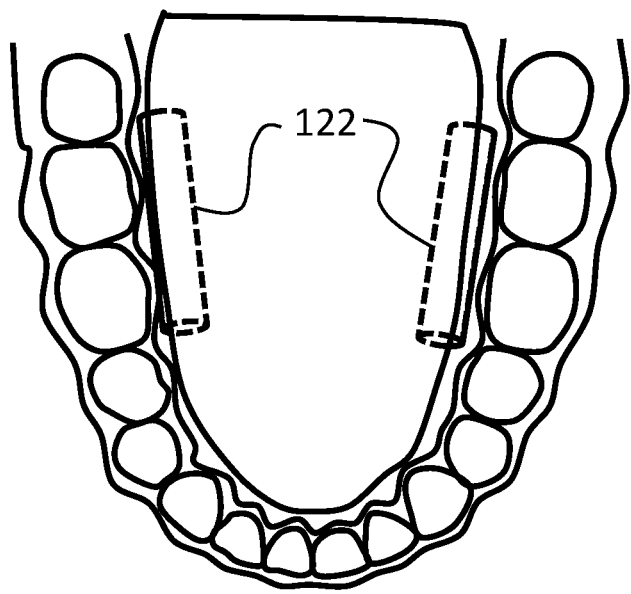
FIG. 28 shows another embodiment of a device comprising a sub-lingual anchor.
Figure 29:
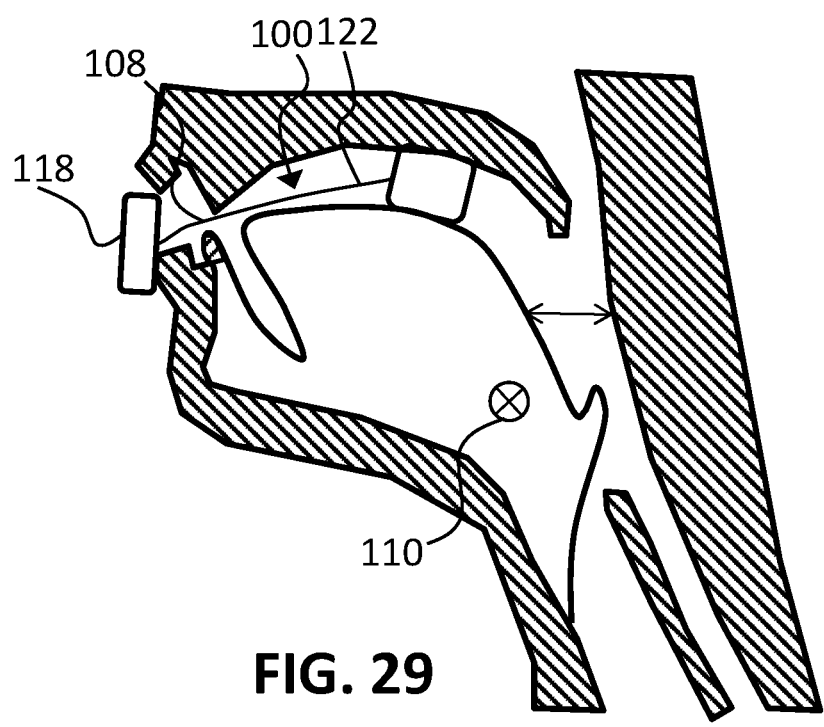
FIG. 29 shows another embodiment of a device comprising a surface anchor.

FIG. 26-29 show embodiments of the present invention that comprise one or more surface anchors (e.g., suction anchors) that can be reversibly attached to a tongue. FIG. 26 shows a U-shaped or curved suction anchor 122 that is located below the tongue. Suction anchor 122 attaches to one or more portions of the ventral side of the tongue to a tissue region inferior to the tongue. In some embodiments, the curvature of suction anchor 122 may be designed or configured to substantially match a curvature of a patient's mouth or jaw. FIG. 27 shows two elongate suction anchor 122 that are located below the tongue as shown. Suction anchors 122 attach, collectively, two or more portions of the ventral side of the tongue to a tissue region inferior to the tongue. The dimensions of each suction anchor 122 may be the same or different, such that the dimensions may be adjusted to achieve the desired tissue displacement or therapeutic effect. FIG. 28 shows two elongate suction anchors 122 that are located below the tongue as shown. Suction anchors 122 attach, collectively, two or more portions of the ventral side of the tongue to a tissue region inferior to the tongue. Suction anchors 122 in FIG. 28 are located more lateral to those in FIG. 27. In FIG. 29, suction anchor 122 has sufficient physical dimensions such that it attaches to a region on the dorsal surface of the tongue and also to a region of the hard palate. Thus, the region on the dorsal surface of the tongue gets mechanically, reversibly fixed to the region of the hard palate.

The location, type, attachment force, vacuum, etc. of any of the suction anchors 122 disclosed herein may be adjusted and/or altered to adjust and/or alter the clinical effect of device 100 comprising the suction anchor 122. Any of the suction anchors 122 disclosed herein may be connected to an element of any embodiment of devices 100 disclosed herein.

Figure 30:
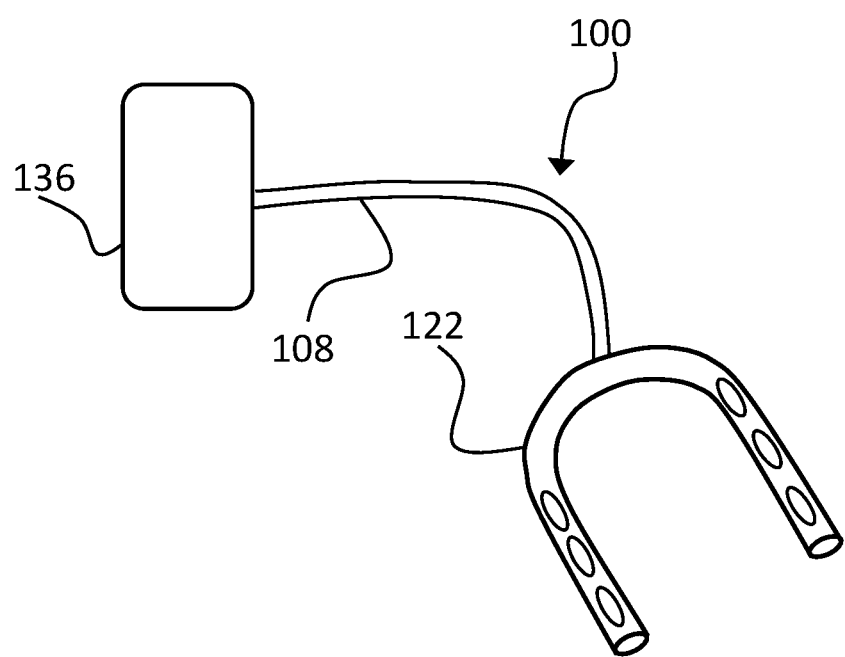
FIG. 30 shows another embodiment of a device comprising a sub-lingual anchor.

FIG. 30 shows a device embodiment of the present invention comprising a suction anchor 122 than can be reversibly attached to a tongue, wherein the suction anchor is connected to a vacuum pump 136. In FIG. 30, suction anchor 122 is connected to a vacuum pump 136 through a first elongate member 108 defining a lumen therethrough. First elongate member 108 is in fluid communication with vacuum pump 136. vacuum pump 136 acts as a vacuum generating element. This embodiment may further comprise a valve e.g., valve 134 of FIG. 24 that can be used to allow or block a fluid communication between vacuum pump 136 and suction anchor 122. The length and other dimensions of elongate member 108 may be such that suction anchor 122 is allowed to extend the tissue to a target displaced position while preventing the tongue from falling too deep into the patient's throat and obstructing the airflow. A size and/or shape of suction anchor 122 may be substantially similar to that of the patient's mouth or jaw. In some embodiments, a size and/or shape of suction anchor 122 is personalized for the patient, such that measurements are taken to determine a best fit between the patient's mouth and the suction anchor 122.

Figure 31:
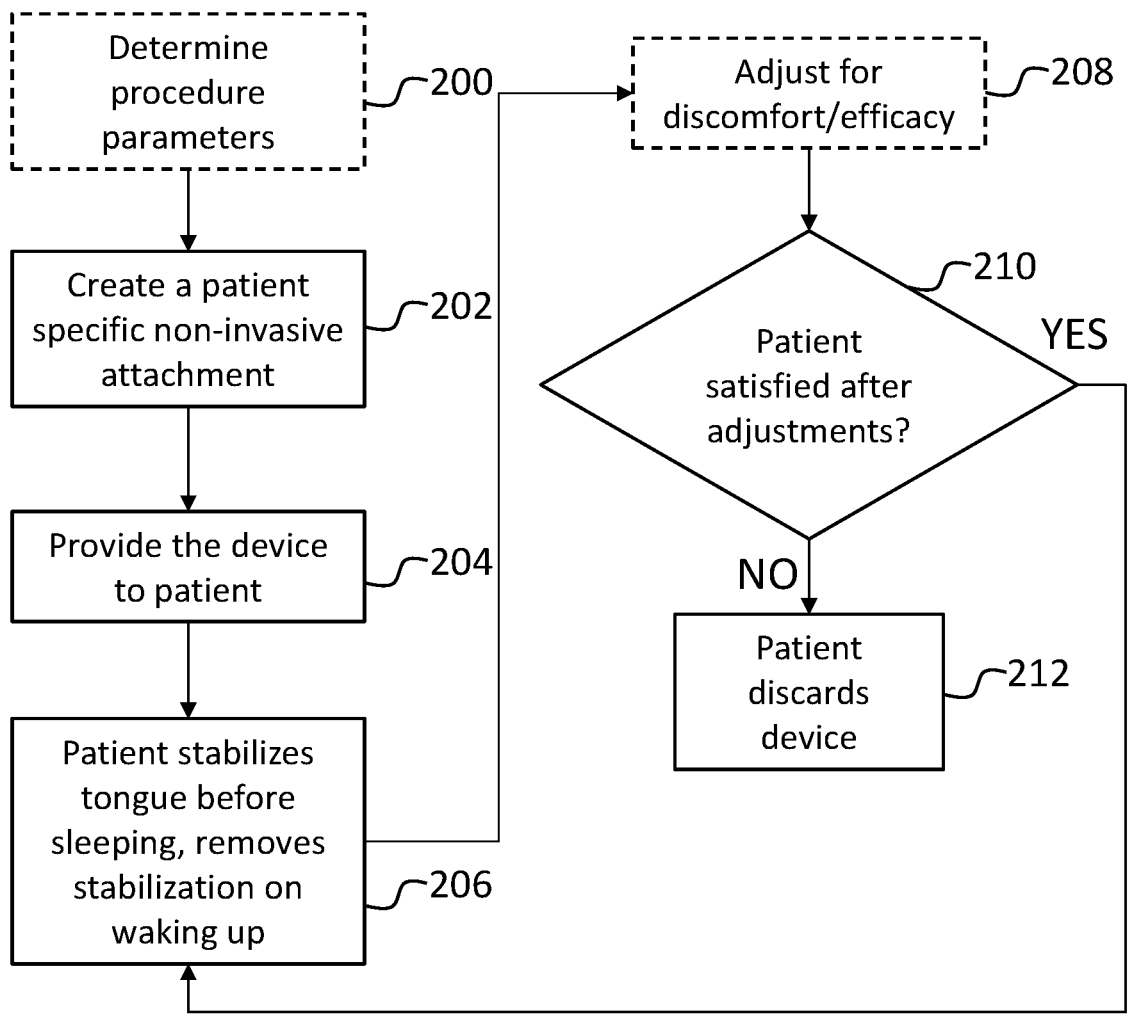
FIG. 31 shows another embodiment of a method of positioning or implanting a device.

FIG. 31 shows an embodiment of a method of the present invention wherein device 100 is non-invasive. At optional step 200, a healthcare provider (e.g., a surgeon, a dentist, etc.) determines one or more parameters of the procedure. Examples of such parameters include, but are not limited to: type (including size) or number of components of device 100 (e.g., suction anchor 122), location of placing one or more anchors, direction of one or more components of device 100, degree of restriction and/or displacement of the tongue, direction and/or magnitude of forces to be applied to the tongue, etc. At step 202, a patient specific non-invasive attachment (e.g., an external anchor 118) is created. Alternatively, a desired attachment may be selected for the patient. At step 204, the device (e.g., combination of one or more components such as suction anchor 122, external anchor 118, one or more elongate members, etc.) is provided to the patient. At step 206, the patient uses the device to stabilize the tongue as disclosed elsewhere herein. At optional step 208, the effect of the device is adjusted for one or more of: comfort/pain, pulling sensation, side effects, and efficacy. At step 210, a determination is made if the patient is satisfied with the procedure and is getting the desired clinical effect. When the patient is satisfied, the patient continues to use the device and the method returns to step 206. When the patient is not satisfied at step 210, the patient may simply discard device 100. A major advantage of the non-invasive methods and devices disclosed herein is that there are no long term or permanent changes to the patient's anatomy. Although the above steps are described sequentially according to the figures, one of skill in the art will appreciate that the steps may be executed in any sequence without departing from the original scope or intent of this disclosure.

Figure 32:
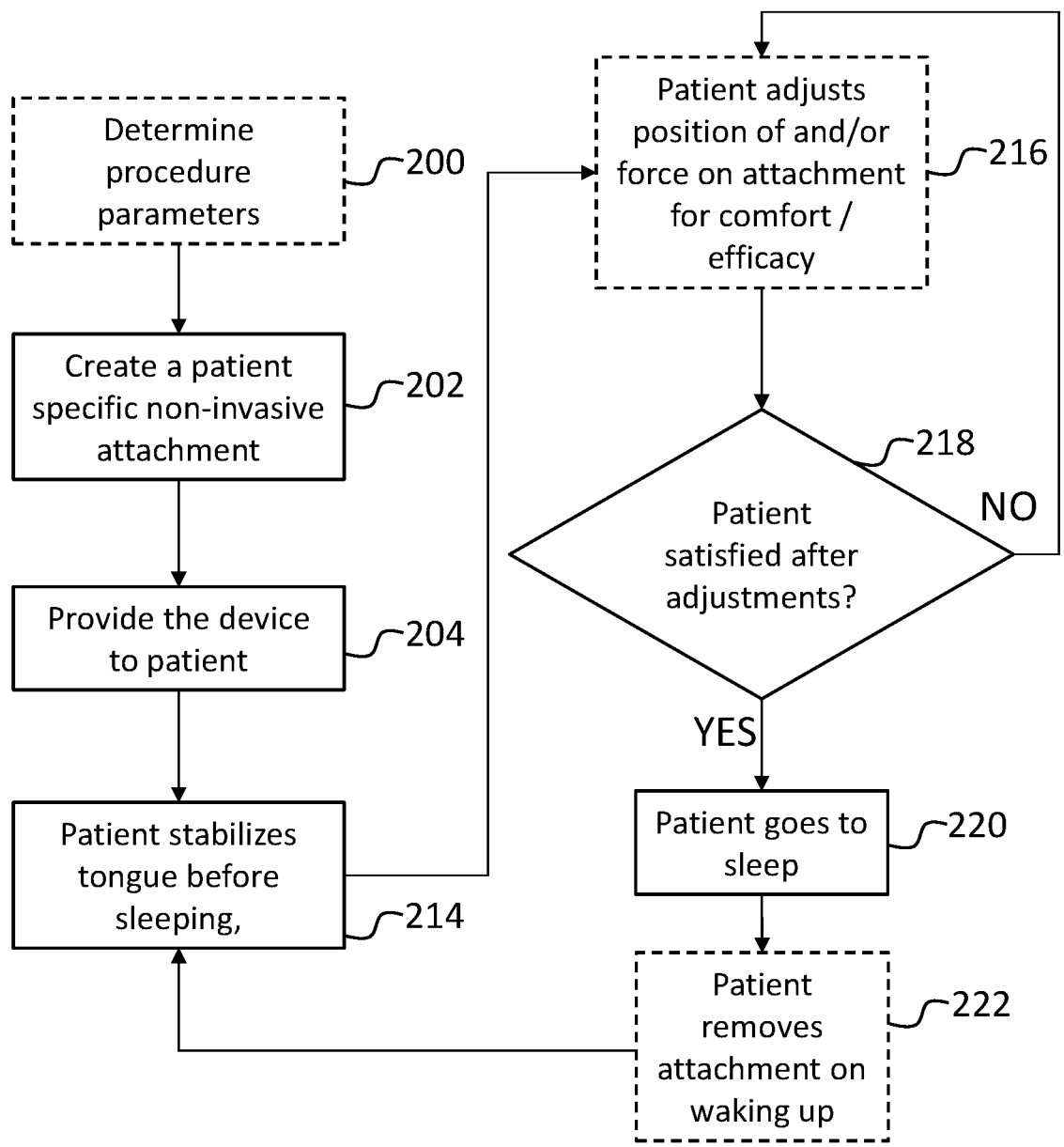
FIG. 32 shows another embodiment of a method of positioning or implanting a device.

FIG. 32 shows another embodiment of a method of the present invention wherein device 100 is non-invasive. Steps 200-204 are similar to those shown in FIG. 31. At step 214, the patient uses the device to stabilize the tongue as disclosed elsewhere herein. At optional step 216, the effect of the device is adjusted for one or more of: comfort/pain, pulling sensation, side effects, and/or efficacy. This may be performed by the patient by adjusting the position of and/or the force on one or more device regions. As described elsewhere herein, any of the devices described herein may be adjusted either by a healthcare provider or by the patient. At step 218, a determination is made if the patient is satisfied with the adjustments. When the patient is not satisfied at step 218, the patient performs additional adjustments. When the patient is satisfied at step 218, the patient continues to use the device and experiences restful sleep. At optional step 222, the patient removes the attachment upon waking (depending on which device was selected for the patient—at least portions of certain embodiments can remain with the patient throughout the day). The method then returns to step 214. Although the above steps are described sequentially according to the figures, one of skill in the art will appreciate that the steps may be executed in any sequence without departing from the original scope or intent of this disclosure.

Figure 33:
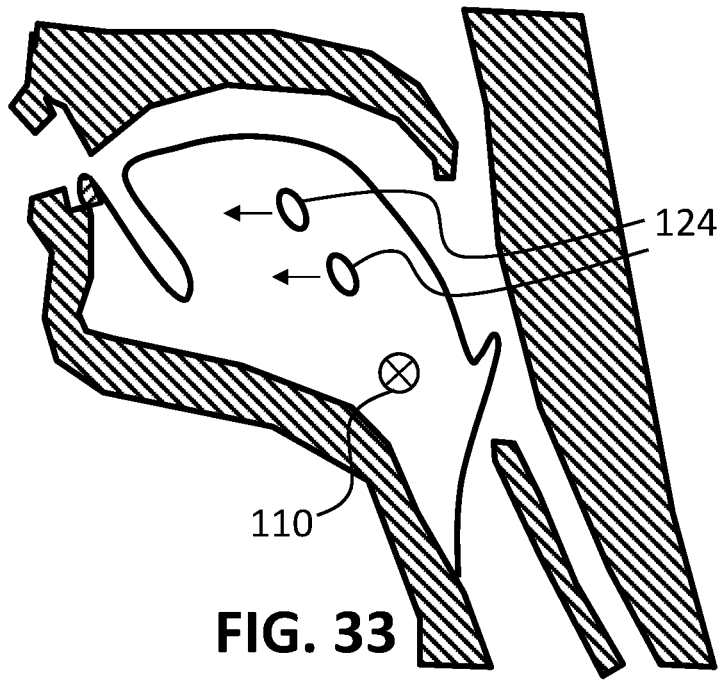
FIG. 33 shows one embodiment of a device comprising a magnet-based anchor.

FIG. 33 shows a section through a human head showing an embodiment of the present invention that comprises magnetic anchors 124. One or more magnetic anchors 124 may be embedded or implanted in or on the tongue. Magnetic anchors 124 may be adjusted by adjusting a magnetic force experienced by the anchors 124. The magnetic force experienced by the anchors 124 may be produced by an external magnet and/or a metallic material. The magnetic force may be adjusted in terms of magnitude and/or direction by varying the position of external magnetic materials. The magnetic force may be adjusted in terms of magnitude and/or direction by varying the position and/or action of external magnets. The adjustment may be performed based on any of the conditions disclosed herein. The adjustment may be performed to achieve any of the clinical effects disclosed herein.

Figure 34:
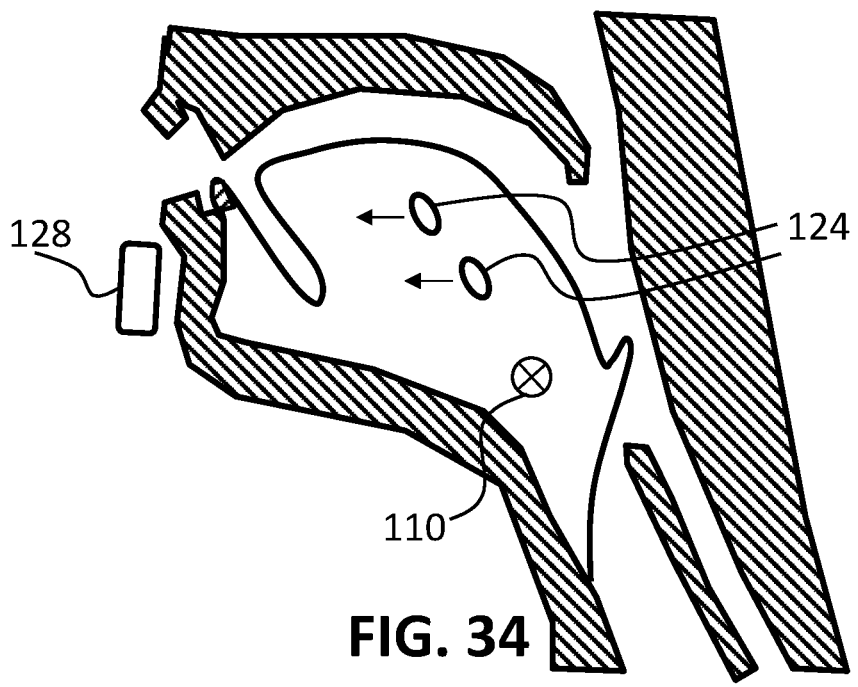
FIG. 34 shows another embodiment of a device comprising a magnet-based anchor.

FIG. 34 shows a section through a human head showing another embodiment of the present invention that comprises magnetic anchors. Magnetic anchors 124 may be adjusted by adjusting a magnetic force experienced by the anchors 124. In this embodiment, the magnetic force is adjusted based on input of sensor 128. The sensor may be coupled to the patient, for example via head gear, face mask, coupled to a bodily portion, etc. The adjustment may be performed based on any of the conditions disclosed herein. The adjustment may be performed to achieve any of the clinical effects disclosed herein.

Figure 35:
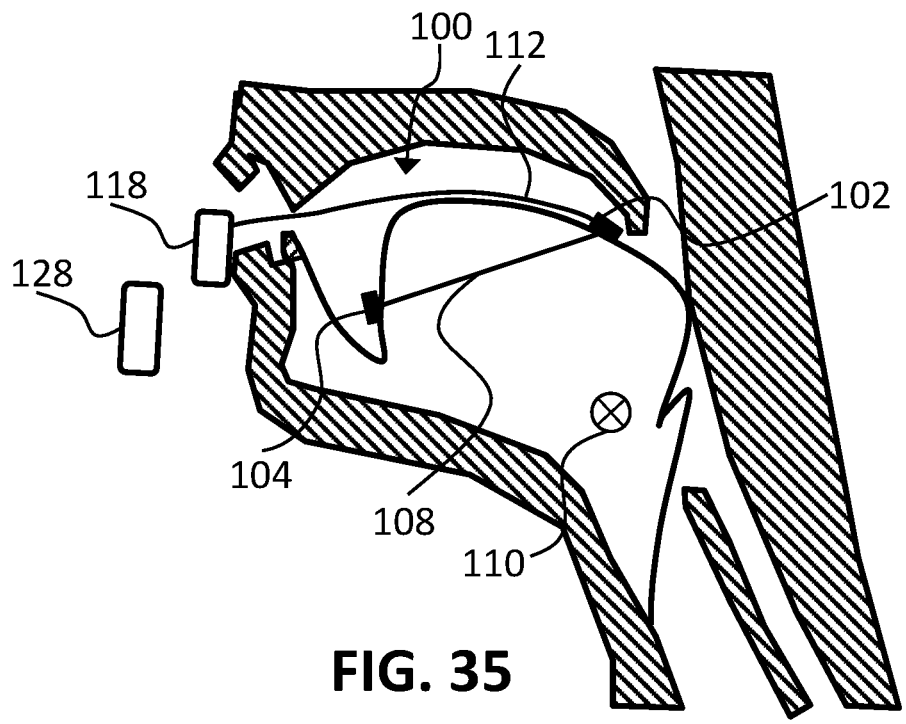
FIG. 35 shows one embodiment of a device that is adjustable based on sensor input.
Figure 36:
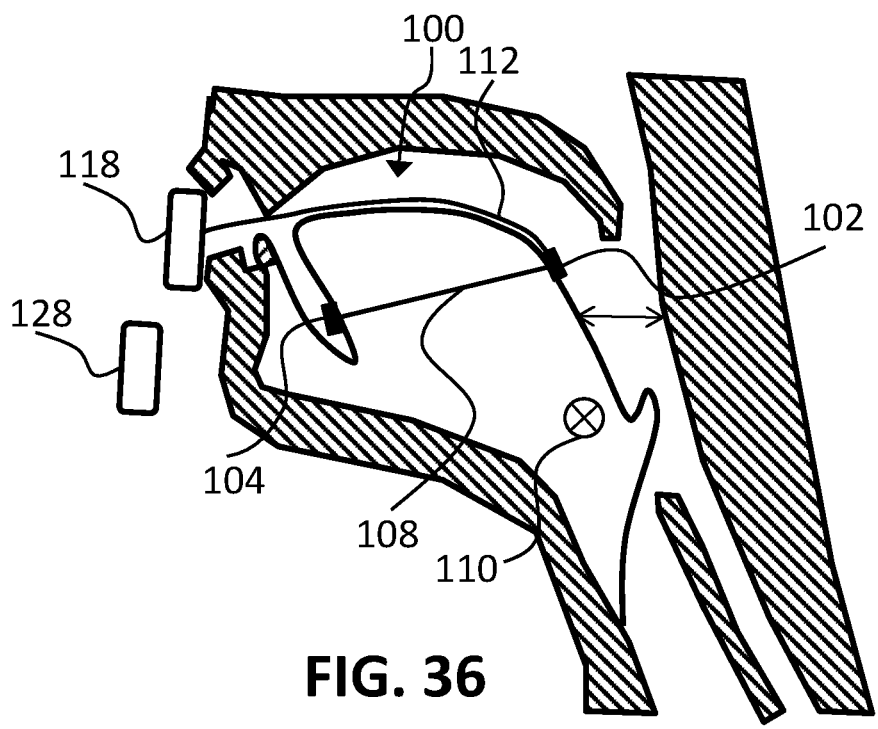
FIG. 36 shows another embodiment of a device that is adjustable based on sensor input.
Figure 37:
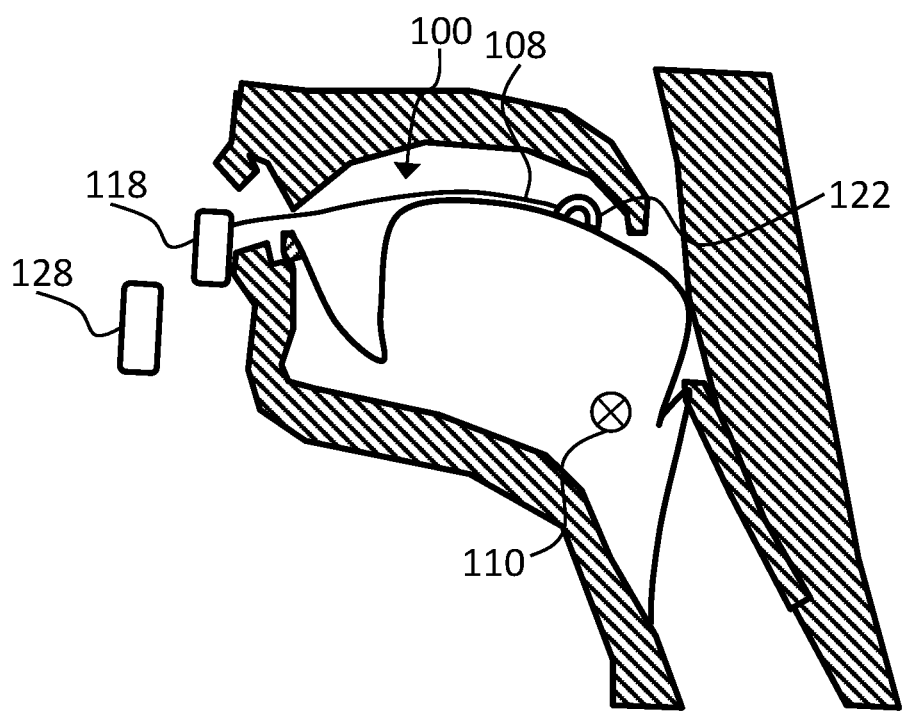
FIG. 37 shows another embodiment of a device that is adjustable based on sensor input.

FIGS. 35-37 show a section through a human head showing embodiments of devices that comprise or otherwise use an external sensor. FIG. 35 shows an embodiment comprising first or dorsal anchor 102, second or ventral anchor 104, and first elongate member 108. First anchor 102 is connected to an external anchor 118 through a second or dorsal elongate member 112. The clinical effect of device 100 can be adjusted using any of the methods herein. Examples of such methods include, but are not limited to: adjusting the tension on second member 112, adjusting the length of an elongate member, adjusting the force on an anchor, etc. The adjustment is made using input from a sensor 128. Any sensor 128 disclosed herein may detect and/or measure one or more parameters comprising one or more of: snoring and other noises, brain activity, eye movement, blood oxygen levels, breathing, sleep apnea, bioimpedance, motion of one or more body regions, orientation of one or more body regions, etc. Any sensor 128 disclosed herein may detect and/or measure one or more parameters throughout the night or throughout the patient's sleep. For example, in response to sensing one or more parameters, the device may be adjusted to improve or otherwise alter a therapeutic effect of the device. Sensor 128 may be located on the face or other bodily regions or may be located near to the patient, e.g., on or near the patient's bed. Sensor 128 may be located on bands around the chest or abdomen, on a film, or on a wearable device. Sensor 128 may comprise one or more microelectronic systems. Specific examples of sensors 128 include, but are not limited to: sensors on Smart Nora™; smart phones loaded with apps such as SnoreLab; sensors located on anti-snore pillows such as Smart Sensor Anti-Snore Pillow; sensors located on SmartSleep Snoring Relief Band made by Philips North America Corporation, Andover, MA; etc.

In FIG. 36, device 100 is adjusted by increasing a pull force, anteriorly, on dorsal anchor 102 by external anchor 118. This may cause the forward displacement of one or more portions of the tongue as seen in FIG. 36. In one embodiment, sensor 128 detects the breathing and/or snoring of the patient. The pull force on anchor 102 is increased when the patient breathes in and is released/reduced when the patient breathes out. In this way, the effect of device 100 is timed to the patient's physiological condition. In another embodiment, sensor 128 detects lowered blood oxygen saturation or sleep apnea. Thereafter, the pull force on anchor 102 is increased to remove one or more airway obstructions (e.g., due to posterior region of the tongue) thereby increasing the patient's blood oxygen saturation. Conversely, the pull force on anchor 102 may be reduced or maintained when the patient's blood oxygen saturation is at a desired level or when sleep apnea is not detected. In another embodiment, sensor 128 detects snoring by the patient. Thereafter, the pull force on anchor 102 is increased to remove one or more airway obstructions (e.g., due to posterior region of the tongue) thereby reducing the patient's snoring. Conversely, the pull force on anchor 102 may be reduced or maintained when snoring is not detected.

FIG. 37 shows an embodiment comprising suction anchor 122 connected to an external anchor 118 through a first or dorsal elongate member 108. The clinical effect of device 100 can be adjusted using any of the methods herein. Examples of such methods include, but are not limited to: adjusting the tension on first elongate member 108, adjusting the length of elongate member 108, adjusting the force on anchor 122, etc. The adjustment is made using input from a sensor 128 through any of the methods disclosed herein.

FIG. 38A shows an embodiment of an implant that is a component of device 100. Such implants may be used with any of the methods and devices disclosed herein. The implant shown in FIG. 38A comprise a first anchor 102 and a second anchor 104 that are connected by a first elongate member 108. In one embodiment, anchor 102 is permanently attached to member 108. Member 108 comprises an attachment mechanism that is used to securely attach second anchor 104 to elongate member 108. In the embodiment shown, the attachment mechanism is a screw mechanism.

FIG. 38B shows an embodiment of an attachment mechanism of device 100. Such attachment mechanisms may be used with any of the methods and devices disclosed herein. The attachment mechanism may be attached to a suitable implant or an anchor shown herein. The attachment mechanism comprises an external anchor 118 that is attached to an elongate member 112. In the embodiment shown, external anchor 118 is designed to be attached to the patient's teeth. For example, external anchor 118 may comprise a mouth guard, bite splint, dental fixture, etc. In the embodiment shown, elongate member 112 is a flexible strap that defines one or more openings or apertures 500. These apertures 500 may be pressed onto an anchor to secure the anchor (e.g., first anchor 102, second anchor 104, etc.) to elongate member 112. The force on the tongue by device 100 and other parameters (examples of which include, but are not limited to distances, displacements, etc.) can be adjusted to multiple levels as per any of the methods disclosed herein by adjusting or altering which aperture 500 that connects to or is coupled to an anchor. Any of the embodiments disclosed herein may be designed to allow multiple levels of adjustment to one or more working parameters. Examples of such working parameters include, but are not limited to: magnitude and/or direction of one or more forces, displacements, distances, locations, etc. For example, devices 100 may be designed such that the length of elongate members between anchors can be adjusted. This adjustment may be performed by the patient. The adjustment may be performed by changing the site of attachment of one or more anchors on an elongate member.

FIG. 38C shows an embodiment of device 100 comprising a non-invasive mechanism for stabilizing the tongue. Such devices 100 may be used with any of the methods and devices disclosed herein. Device 100 comprises an external anchor 118 that is attached to an elongate member 112. In the embodiment shown, external anchor 118 is designed to be attached to the patient's teeth. In the embodiment shown, elongate member 112 is a flexible strap that defines one or more openings or apertures 500. These apertures 500 may be pressed onto one or more suction anchors 122 to secure anchor attachment 502 to member 112. The force on the tongue by device 100 can be adjusted as per any of the methods disclosed herein by adjusting or altering which aperture 500 connects to an anchor 122. Any suitable embodiments disclosed herein such as the embodiment of FIG. 38C may be designed as a single integrated device wherein the components of device 100 that are placed on bodily regions do not physically separate from each other. This design reduces the risk of component separation and choking during use. In one such embodiment, suction anchor 122 has an attachment (e.g., mechanical connector(s), strings, wires, etc.) to elongate member 112 which allows repositioning of suction anchor 122 on various apertures 500 but prevents physical separation of suction anchor 122 from the rest of device 100 even if suction anchor 122 is separated from an aperture 500.

Device embodiments disclosed herein may be designed to reduce or eliminate the hazard of triggering a gag or producing a choking hazard during use. In one such embodiment, additional mechanical connections are provided that connect one or more components of device 100. For example, in embodiments comprising two anchors connected by an elongate member, a separate mechanical connector may be provided that connects the two anchors. In case the elongate member breaks, the anchors mechanically will still remain connected through the mechanical connector. The mechanical connector may have a higher strength than the elongate member. The mechanical connector may be longer than the elongate member. In another embodiment, elongate members and/or one or more connections disclosed herein may be reinforced for extra mechanical strength. Examples of reinforcements include, but are not limited to: metallic materials such as wires embedded in or otherwise attached to device components, use of thicker materials, use of coating(s) that reinforce device components, etc. In another embodiment, device 100 is designed such that a loss of function occurs before mechanical separation of one or more components. For example, loss of function may be felt through one or more of: loss of vacuum/suction, loss of a force, loss of a clinical action, etc. before mechanical separation occurs. In one specific example, breakage of an elongate member 108 causes a vacuum loss before complete breakage of elongate member.

Device embodiments disclosed herein may be designed to reduce or eliminate the hazard of triggering a gag or producing a choking hazard during use.

Figure 39:
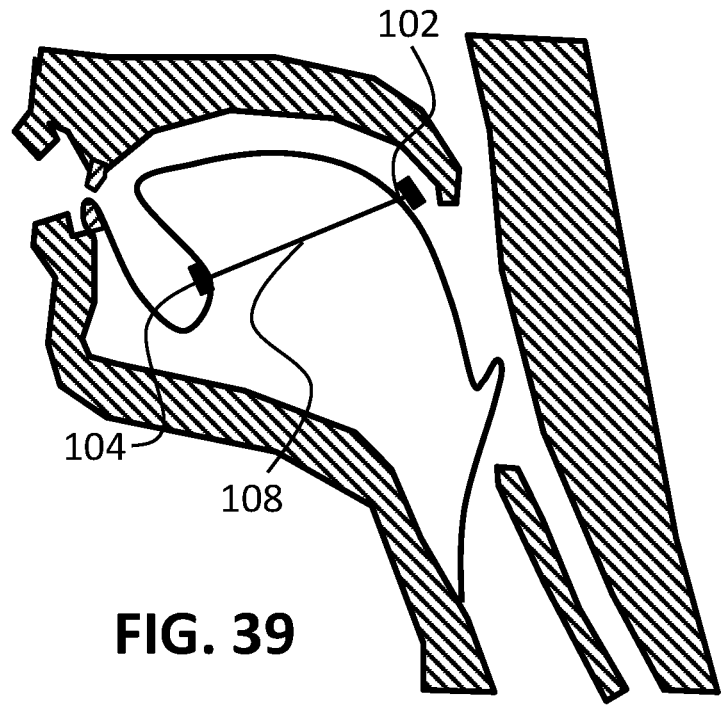
FIGS. 39-42 show various steps of a method of applying a displacement force to a tongue using a tongue anchor-based device.
Figure 40:
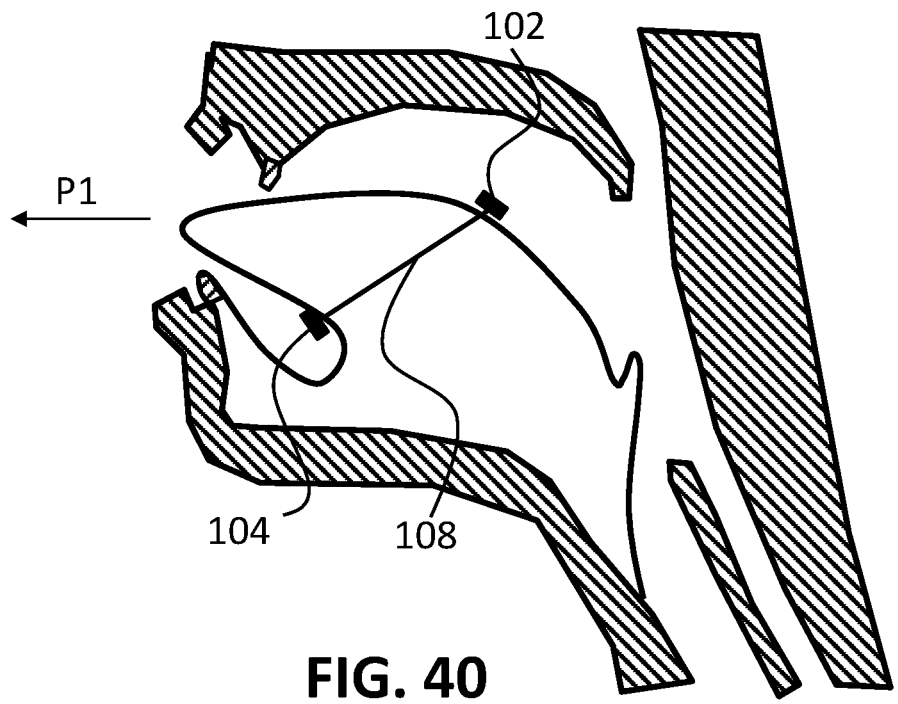
Figure 41:
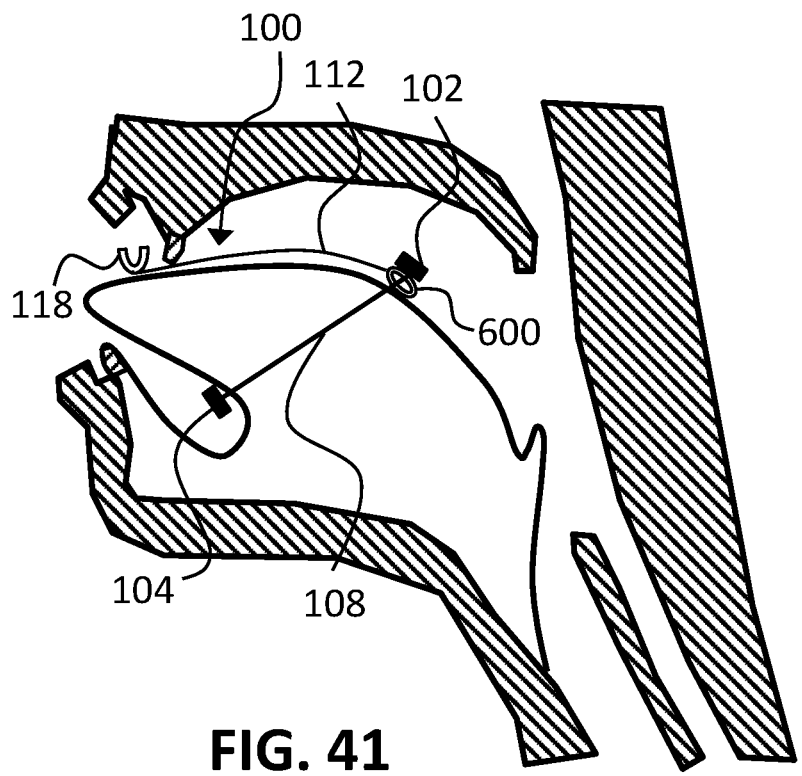
Figure 42:
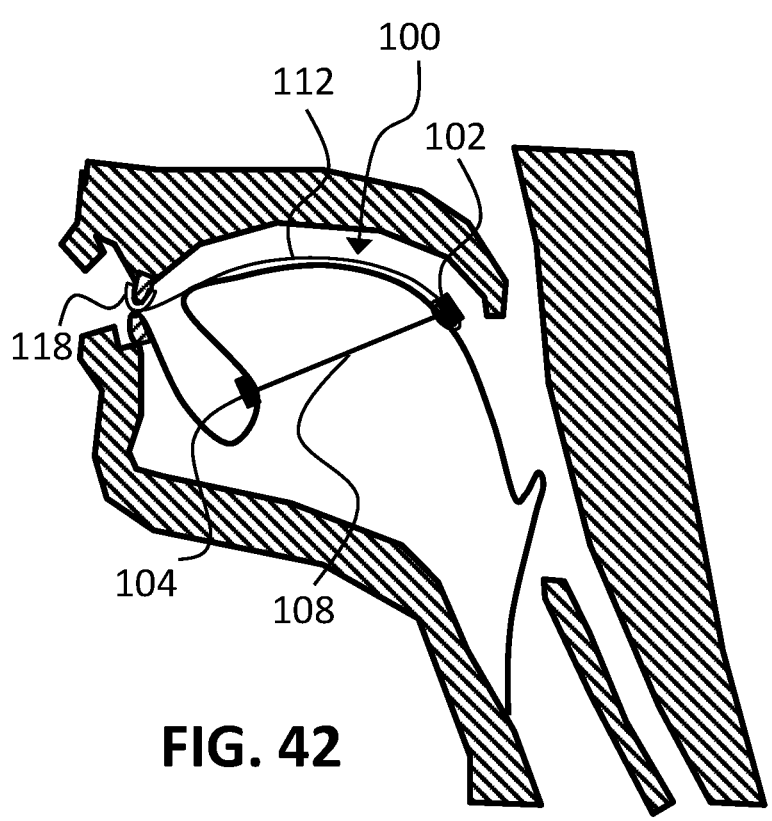

FIGS. 39-42 show an embodiment of a method of reversibly stabilizing the tongue. This may be used, for example, when the patient is going to sleep and wants to keep the airway open. FIG. 39 shows the normal resting position of the tongue. In FIG. 40, the patient pulls the tongue forward, shown as arrow P1, so that a first or dorsal anchor 102 is made more accessible to the attachment shown in FIG. 41. In FIG. 41, an attachment is inserted into the mouth. The attachment comprises an external anchor 118 connected to a coupling element 600 (e.g., loop, lasso, hook, clip, etc.) via a second or dorsal elongate member 112. The patient connects the coupling element 600 to the implant of FIG. 40 (e.g., via first or dorsal anchor 102). This may be performed, by example, by attaching coupling element 600 to first anchor 102. Thereafter, in the step shown in FIG. 42, external anchor 118 is connected to a region of the patient's upper or lower teeth. This stabilizes the tongue and prevents the tongue from falling posteriorly when the patient is asleep. The patient may then relax the tongue and go to sleep. When the patient wakes up and no longer needs the tongue stabilization, the tongue is advanced forward and coupling element 600 is detached from first anchor 102. External anchor 118 is detached from the patient's teeth and the attachment is removed from the patient's mouth.

In any of the embodiments herein, one or more anchors such as first anchor 102 and second anchor 104 may be designed and/or positioned such that one or more anchors or each anchor is physically separated by a distance from the tissue boundary. Thus, there may be a physical gap between an anchor and the tissue in the working position of the device. This allows the patient to easily attach elements such as coupling element 600 to the anchors.

In any of the embodiments herein, one or more anchors such as first anchor 102 and second anchor 104 may be designed and/or placed such that the anchors are easily accessed by the patient without needing to reach deeply inside the mouth or without producing a gag reflex. This may be achieved by placing the anchors at accessible regions such as the tongue body and avoiding regions such as the tongue base. This placement allows the patient to easily attach elements such as coupling element 600 to one or more anchors.

Figure 43:
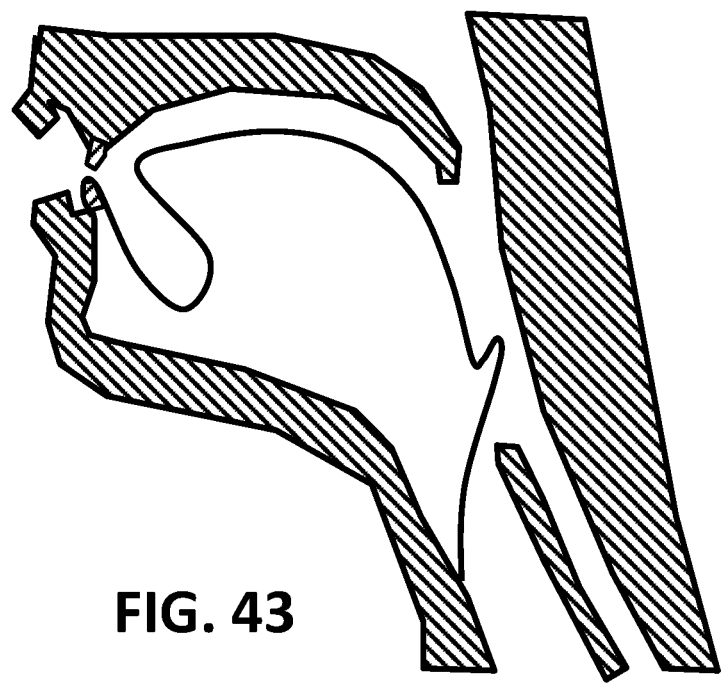
FIGS. 43-46 show various steps of a method of applying a displacement force to a tongue using a surface anchor-based device.
Figure 44:
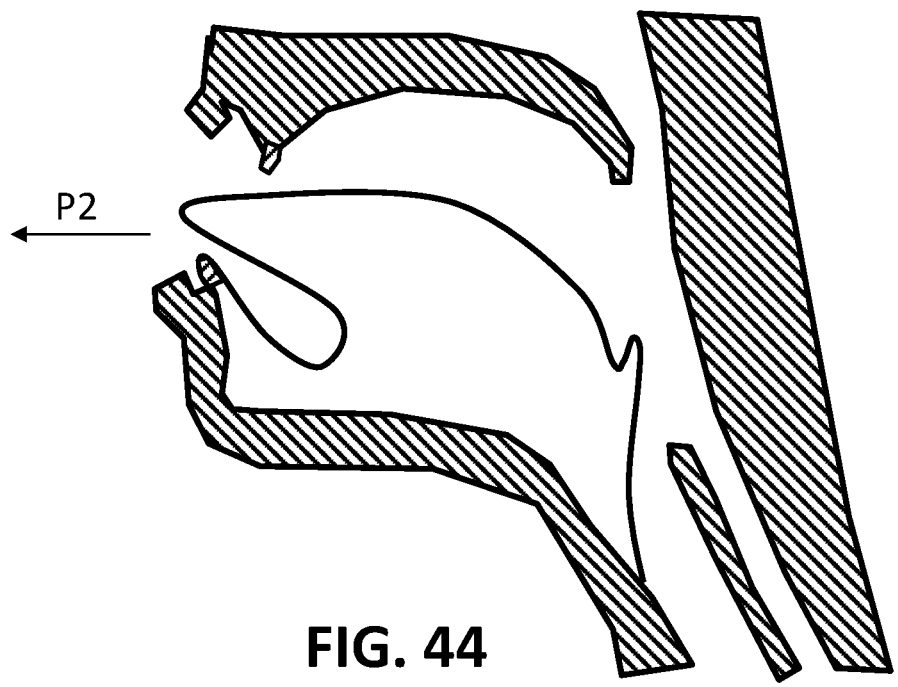
Figure 45:
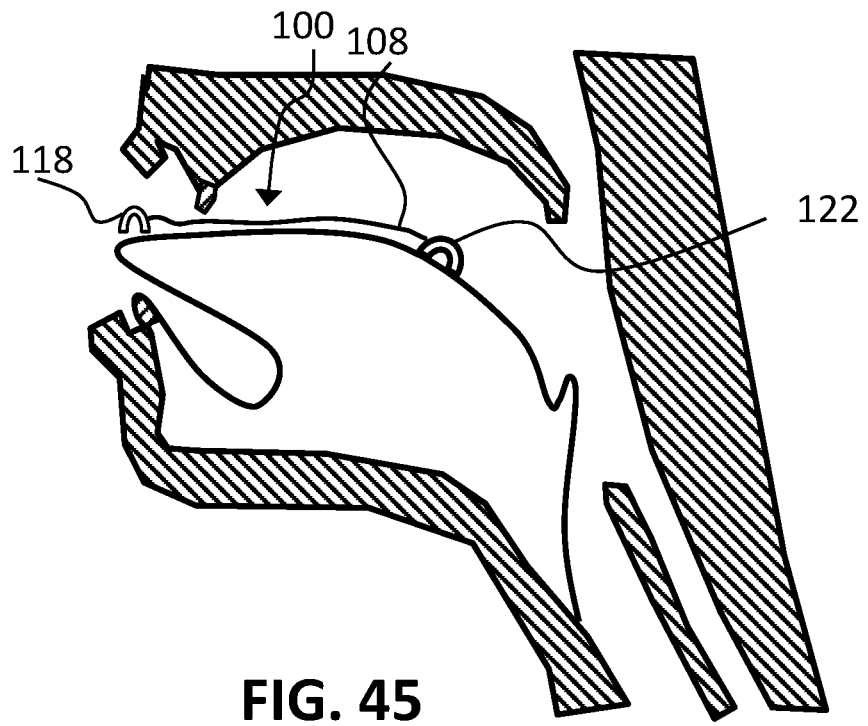
Figure 46:
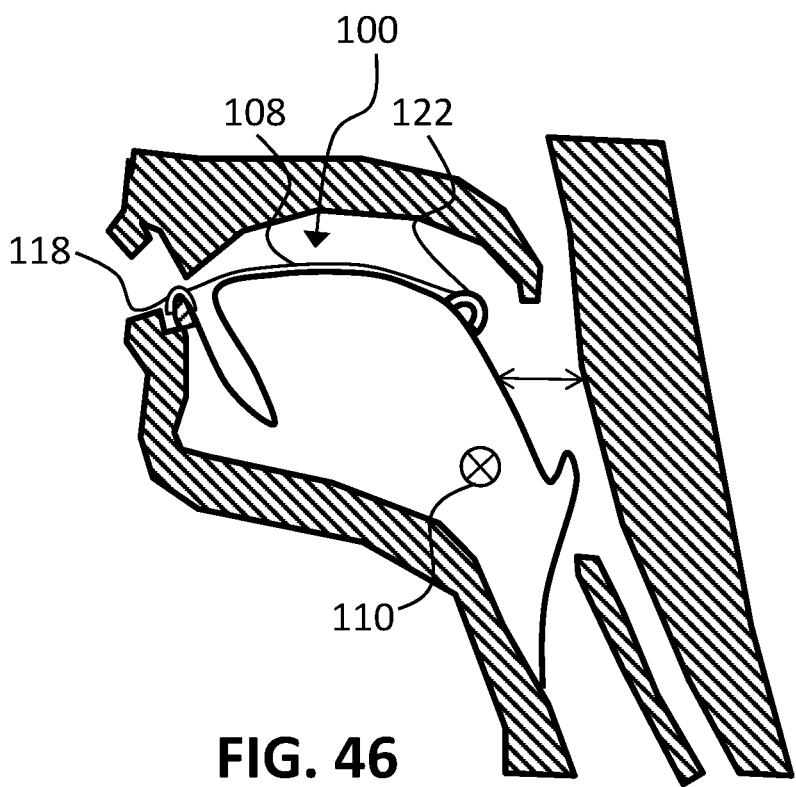

FIGS. 43-46 show one embodiment of a method of reversibly stabilizing the tongue using a non-invasive device. This may be used, for example, when the patient is going to sleep and wants to keep the airway open. FIG. 43 shows the normal resting position of the tongue. In FIG. 44, the patient pulls the tongue forward, shown as arrow P2, so that the target location of the tongue for suction anchor 122 is made more accessible. In FIG. 45, device 100 is inserted into the mouth. Device 100 comprises an external anchor 118 connected to a suction anchor 122 through a first elongate member 108. The patient attaches suction anchor 122 to the tongue using any suitable method, examples of which are disclosed elsewhere herein. In the step shown in FIG. 46, external anchor 118 is connected to a region of the patient's lower or upper teeth. This stabilizes the tongue and prevents the tongue from falling posteriorly when the patient is asleep. The patient may then relax the tongue and go to sleep. When the patient wakes up and no longer needs the tongue stabilization, the tongue is advanced forward and suction anchor 122 is detached from the tongue. External anchor 118 is detached from the patient's teeth and device 100 is removed from the patient's mouth.

Figure 47:
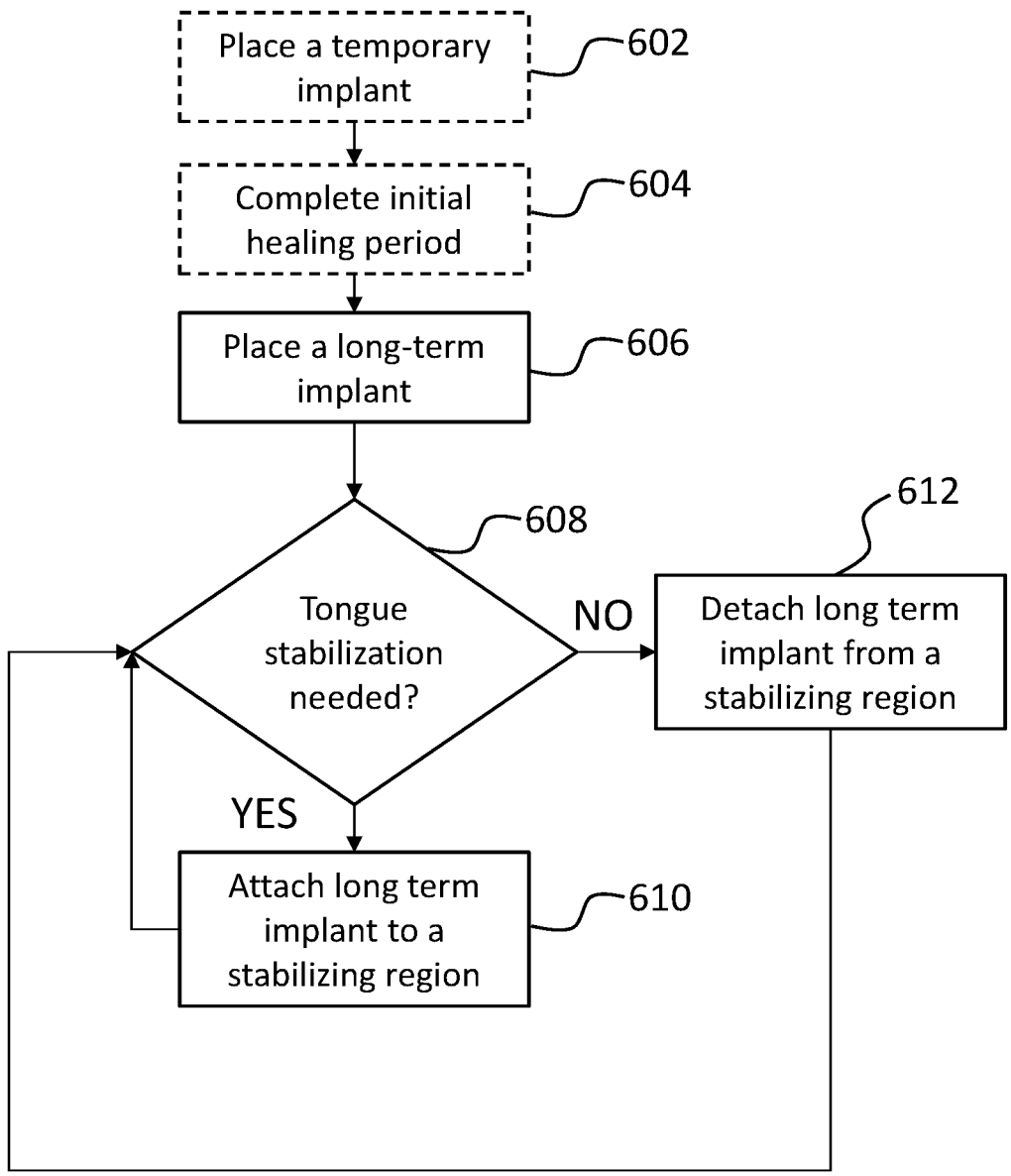
FIG. 47 shows one embodiment of a method of stabilizing a tongue of a patient.

FIG. 47 shows an embodiment of a method for reversibly stabilizing the tongue when needed and removing the stabilization when not needed. At optional step 602, a temporary implant is placed as disclosed elsewhere herein. At optional step 604, an initial healing period is completed as disclosed elsewhere herein. At step 606, a long-term implant is placed as disclosed elsewhere herein. At step 608, the user determines when tongue stabilization is needed. When tongue stabilization is needed, at step 610, the long-term implant is attached to a stabilizing region (e.g., the patient's teeth). When tongue stabilization is not needed, at step 612, the long-term implant is detached from the stabilizing region so that it does not interfere with the normal tongue functions like tasting, talking, eating, etc. In this way, an "on-demand" tongue stabilization action may be used to improve the airflow through the airway.

Figure 48:
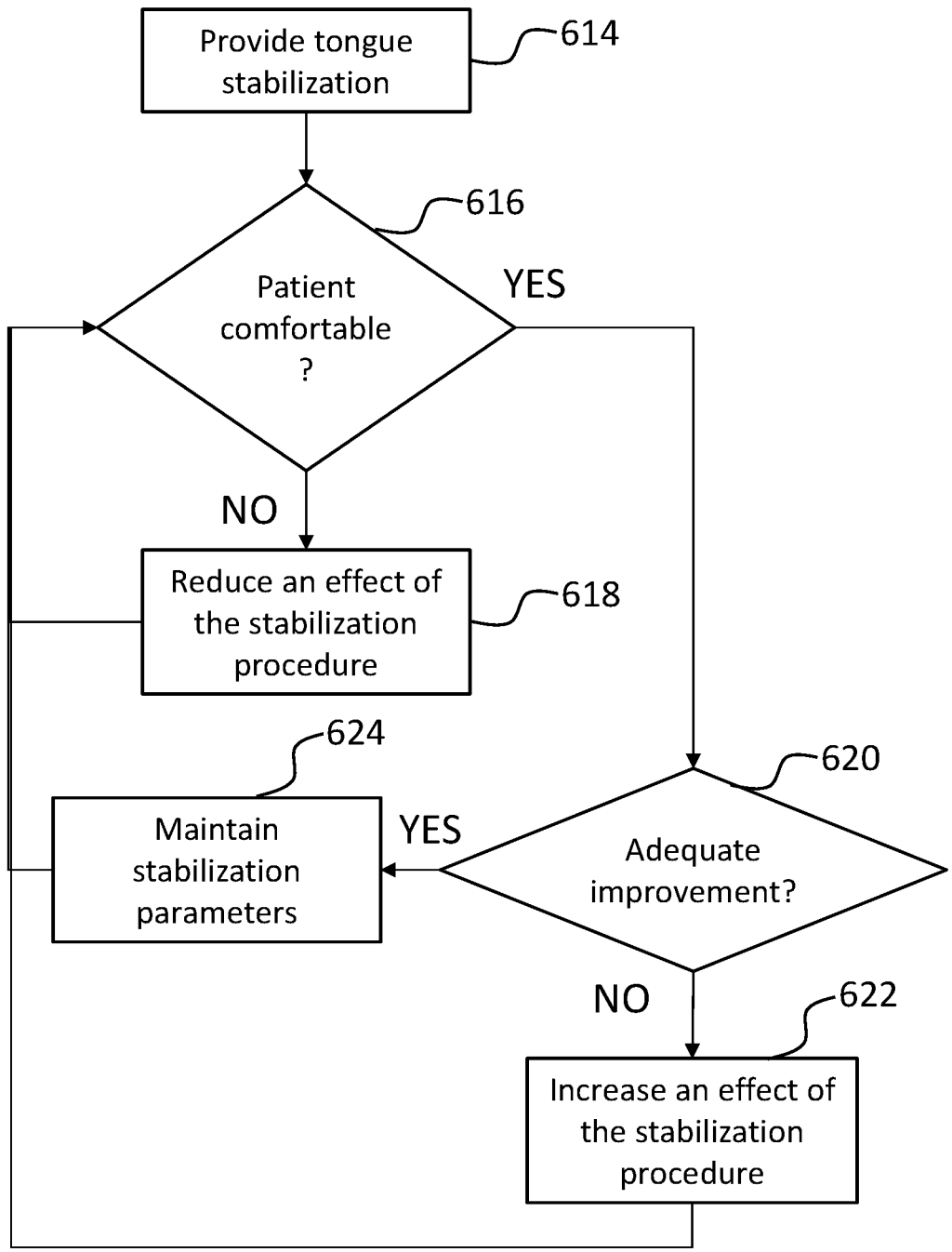
FIG. 48 shows another embodiment of a method of stabilizing a tongue of a patient.

FIG. 48 shows an embodiment of a method for adjusting a stabilizing effect on the tongue. At step 614, a method described herein is used to provide tongue stabilization. At step 616, the patient determines when the tongue stabilization is comfortable. When it is comfortable, the patient determines when the improvement in symptoms due to tongue stabilization is adequate. In one such embodiment, the patient determines when the improvement in snoring is adequate. In one such embodiment, the patient determines when the improvement in sleep apnea is adequate. In one such embodiment, the patient determines when the improvement in a sleep or respiration parameter is adequate. when the improvement is not adequate, the effect of the stabilization procedure is increased at step 622. For example, this effect may be increased by increasing a stabilization force on the tongue. The method then proceeds back to step 616. When the improvement is adequate, the stabilization parameters (including, but not limited to: type of device 100, locations of one or more components of device 100, forces on the tongue, etc.) are maintained and the method returns to step 616. When at step 616, the patient determines that the tongue stabilization is not comfortable, the effect of the stabilization procedure is reduced at step 618. For example, this effect may be reduced by reducing a stabilization force on the tongue.

Figure 49:
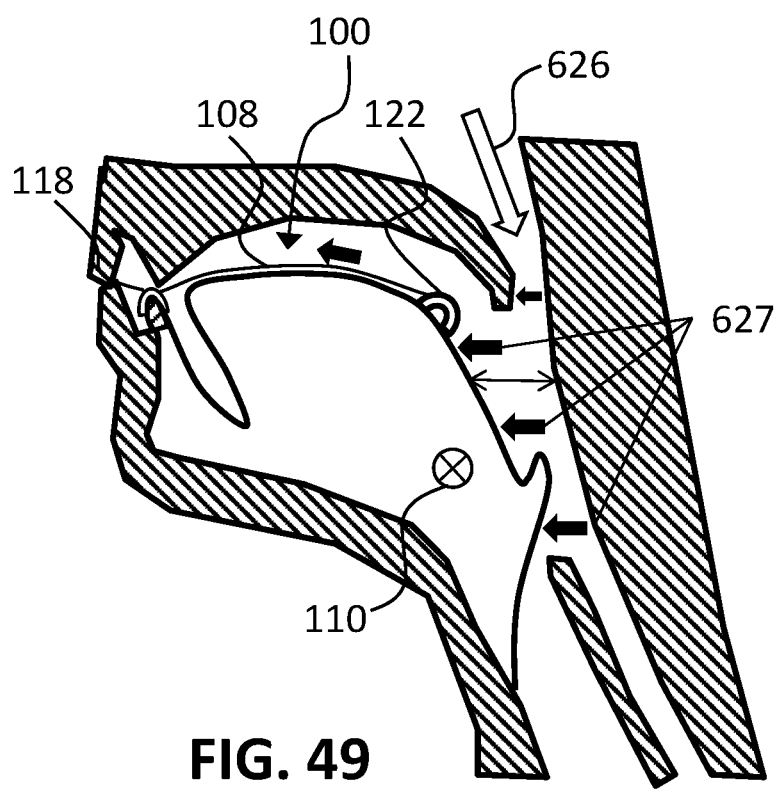
FIG. 49 shows a combination embodiment that includes an implant and positive airway pressure.

Any of the embodiments disclosed herein may be used in combination with any modality that generates a positive airway pressure; examples of which include, but are not limited to: Continuous Positive Airway Pressure (CPAP) systems and nasal resistance devices. In such combination embodiments, forces are applied on the tongue and other anatomical regions from: the devices disclosed herein and/or the positive pressure acting on tissue surfaces. FIG. 49 shows an embodiment of a method of treating a patient using an embodiment disclosed herein in combination with positive airway pressure. The open arrow 626 in FIG. 49 shows the direction of the airflow and the solid arrows 627 show the forces exerted on the tongue and soft palate. As shown in FIG. 49, the positive airway pressure creates an anterior displacement force on one or more of: tongue regions and soft palate regions. Also, the tongue interventions (any disclosed herein although a suction anchor is shown) disclosed herein create a displacement force on one or more tongue regions. This displacement force comprises an anterior component. Thus, in such combination embodiments, the forces act on the soft palate and also on the tongue. This may improve sleep disordered breathing. The combination embodiments are especially useful in obese patients and in patients where the soft palate is also contributing to snoring or OSA. Such combination embodiments may create a synergistic effect that keeps the airway open. One or more tongue interventions disclosed herein may be used to prevent or reduce the tongue from falling back on (i.e., exerting a posterior force on) portions of the soft palate. When these forces are prevented or reduced, posterior displacement of the soft palate is also prevented or reduced. A positive airway pressure modality can then act on the soft palate and easily displace the soft palate anteriorly. This synergistic effect means that the forces needed to splint the airway open by displacing portions of the soft palate and/or the tongue are significantly reduced. This in turn means that the positive airway pressure modality can achieve its desired effect even with lower airway pressures. This significantly increases the tolerability and patient acceptance of such modalities.

In one method embodiment, a tongue device is placed on or implanted on the patient's tongue. Thereafter, a patient starts the action of a tongue device. Several examples of such procedures and actions are listed in this specification. The patient then turns on the positive airway pressure modality. The effect of the combination procedure may be adjusted based on one or more of: efficacy and tolerability of the combination procedure. One or more parameters of the combination procedure may be adjusted based on the above. Examples of such parameters include, but are not limited to: forces applied on the tongue, location of one or more device portions on the tongue, location of one or more external anchors, lengths of one or more connectors, pressure levels, etc. The combination procedures may be used for gradually weaning the patient off or tapering off one or more treatments. In one embodiment, a combination procedure starts with a larger force on the tongue and a lower airway pressure. Thereafter, the force on the tongue and/or airway pressure is adjusted for increased efficacy and/or tolerance. In one embodiment, a combination procedure starts with a smaller force on the tongue and a higher airway pressure. Thereafter, the force on the tongue and/or airway pressure is adjusted for increased efficacy and/or tolerance. Eventually, a combination procedure may transition to only a single mechanism—tongue displacement or positive airway pressure.

Figure 50:
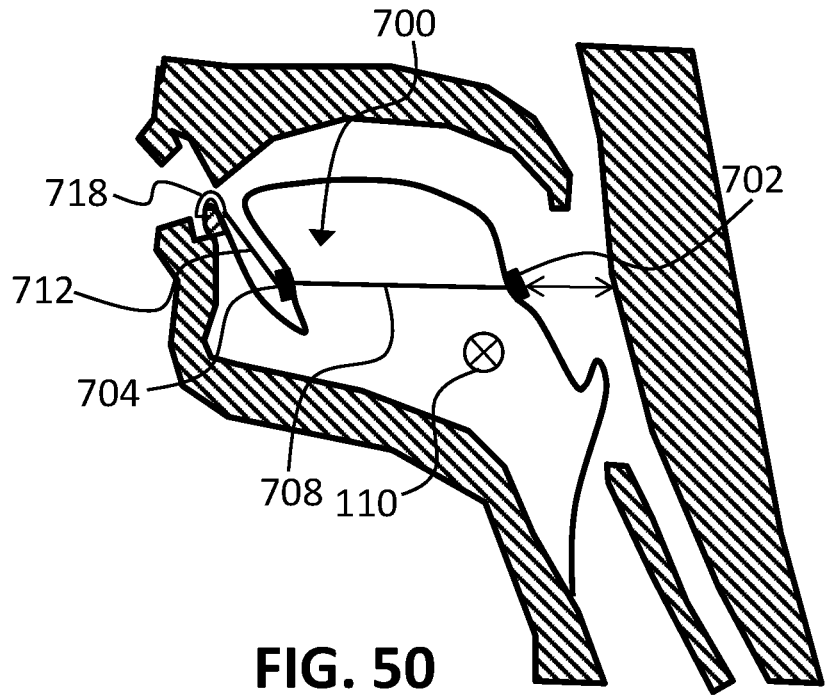
FIG. 50 shows one embodiment of a device configured for positioning at a tongue base.
Figure 51:
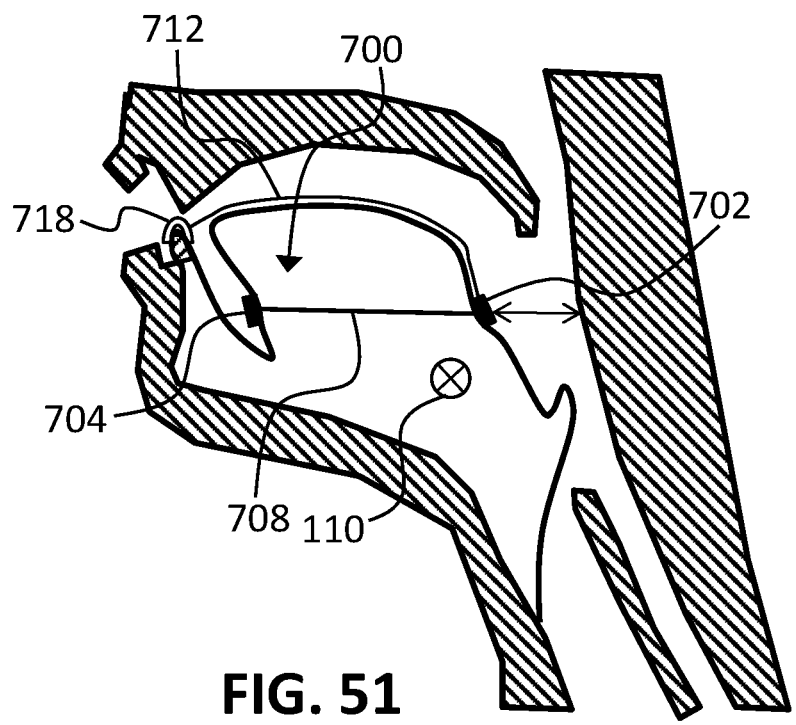
FIG. 51 shows another embodiment of a device configured for positioning at a tongue base.

FIGS. 50-51 show two embodiments, respectively, of devices 700 of tongue stabilization that also compress one or more regions of the tongue base. In FIGS. 50-51, the tongue base has been compressed using an implant comprising a first tongue base anchor 702, a first elongate member 708, and a second anchor 704. In FIG. 50, an attachment comprising an external anchor 718 (connected to the lower teeth) and a second elongate member 712 (connected to second anchor 704) are used to stabilize the tongue. In FIG. 51, an attachment comprising an external anchor 718 (connected to the lower teeth) and a second elongate member 712 (connected to first tongue base anchor 702) is used to stabilize the tongue. Examples of such attachments are disclosed elsewhere herein. Examples of methods and devices to compress one or more regions of the tongue base are disclosed in US patent publication no. 20200069320; U.S. Pat. No. 10,195,010; and US patent publication no. 20200330262; the entire disclosures of each of which are incorporated herein by reference. Such compression devices may be attached to attachment devices disclosed herein using methods disclosed herein to provide tongue stabilization in addition to tongue compression.

The force generated by any of the embodiments herein may be sufficient to displace a portion of the tongue and/or supraglottis to reduce the resistance to airflow at the level of the oropharynx or hypopharynx.

Various methods that can be used to diagnose/identify patients suitable for this invention include, but are not limited to: imaging, pressure transducer recording acoustic analysis, and endoscopic evaluation. Such methods may also be used for procedure planning (e.g., determining the type and locations of one or more anchors, size/length of one or more elongate members, tension/pull force on one or more components of device 100, forces on tongue, etc.). In such embodiments, a sleep condition may be simulated in a patient to simulate one or more effects of the sleep state. Examples of such effects include, but are not limited to: head position and/or orientation, lack of muscle tone in the tongue, lack of muscle tone in or more structures of the airway anatomy, etc. Drug Induced Sleep Endoscopy (DISE) is an example of an endoscopic evaluation that may be used for identifying the anatomical region responsible for obstructing the upper airway and/or procedure planning. In one such embodiment, DISE (or other suitable method(s)) is used to determine the effect of any of the temporary implants described herein. Based on the information obtained during the placement of the temporary implant, further procedures can be planned. For example, more invasive or permanent procedures can be planned and performed. In some instances, as used herein, temporary implants may include surface or suction implants; and long-term or invasive implants include anchored implants, for example with tissue penetrating elements or that pass through at least a portion of the tongue tissue. However, as compared to currently available remedies, all embodiments described herein can be viewed as temporary and/or reversible since they do not substantially alter a patient's anatomy. The placement of the temporary implant can be used to determine one or more parameters of the further procedure(s). Examples of such parameters include, but are not limited to: type/location/size of one or more anchors, type/length/location of one or more elongate members, etc.

One or more portions of device 100 may comprise means for providing one or more stimuli to the tongue or other portions of the anatomy. Examples of such stimuli include, but are not limited to: thermal stimulus, vibrations or other mechanical stimulus, electrical stimulation (e.g., neurostimulation), etc. Such stimuli may be used for functions including, but not limited to: creating contraction of one or more portions of the tongue, displacing tongue portions away from posterior pharynx, increasing the tone or one or more tongue regions, rousing the patient, changing the state of consciousness or sleep of the patient, etc.

Any of the devices herein or portions of the devices herein including, but not limited to magnetic element, may be encapsulated by one or more biocompatible layers that increase the biocompatibility of one or more portions of the implant.

In any of the embodiments herein, one or more portions of the tongue and other tissue may be temporarily stabilized to enable the introduction and/or the placement of one or more portions of device 100. Examples of devices that may be used for such stabilization include, but are not limited to: clamps, suction based tools, e.g., suction cups, elongate penetrating elements, and a part of device 100.

In one method embodiment, a temporary device 100 is implanted during the immediate post-operative phase. Thereafter, a sufficient time is allowed for the post-operative swelling to reduce. Thereafter, using the implant tract of temporary device 100, a long-term device 100 is implanted in the anatomy. Thereafter, long-term device 100 may be adjusted using any of the methods disclosed herein to adjust a clinical effect on the patient.

The steps of one method embodiment of the present invention are as follows: the user (e.g., physician, surgeon, nurse, or other operator) checks the patient for suitability of the procedure. Thereafter, the user administers anesthesia or analgesia to the patient. The user checks the tongue for location of large blood vessels. Devices 100 and other elements of the present invention, e.g., penetrating element 120, are preferably placed in regions of the tongue that lacks major blood vessels. The site(s) of the penetration and/or one or more portions of device 100 may be marked. Thereafter, the user mechanically secures the tongue, e.g., using tools like graspers, forceps, etc. and orients one or more portions of the tongue in a desired orientation. Thereafter, the tongue is punctured to insert one or more portions of the invention such as devices 100, penetrating element 120, etc. The tongue puncture may be initiated from one of dorsal, ventral, and lateral surfaces of the tongue and may extend to one of dorsal, ventral, and lateral surfaces of the tongue. The puncture may or may not extend through the full thickness of the tongue. The puncture may be performed with needles, cannulas, stylets, penetrating elements 120 or portions of devices 100. After placing devices 100, the patient may be administered one or more medications such as steroids or anti-inflammatory drugs to reduce the immediate post-procedure swelling. One or more portions of devices 100 may be coated or otherwise comprise one or more medications (including, but not limited to: steroids or anti-inflammatory drugs) to reduce the immediate post-procedure swelling. Devices 100 disclosed herein may be adjusted one or more times after the initial implantation. Examples of adjustment include, but are not limited to: changing the type, number, or location of one or more anchors; changing the type, location, length of one or more elongate members; changing one or more forces on the tongue; changing the degree of rotation of one or more portion of the tongue around rotation axis 110; and/or changing the degree of restriction to motion of one or more portions of the tongue. The length of one or more elongate members (for example, the length of an elongate member between two anchors) may be reduced after the initial procedure (for example, after two to 180 days post-procedure) to adjust device 100 for reduction in post-procedure swelling. In one embodiment, the reduction in length is between about 2 mm to about 35 mm.

One or more anchors disclosed herein may be placed through a piercing in the mid-line of the tongue. The location of an anchor may be about 2 cm; about 1.5 cm; about 2.5 cm; about 1 cm to about 2 cm; about 1.5 cm to about 2.5 cm; about 1 cm to about 3 cm; etc. or more posterior to the tip of the tongue. The location of circumvallate papillae or other anatomical regions may be used as a marker to determine the placement of any incision, penetration path, or anchor disclosed herein. In one such embodiment, one or more anchors are placed anterior to the circumvallate papillae. One or more anchors disclosed herein may be placed in the anterior third of the tongue. One or more anchors disclosed herein may be placed in regions to avoid gag reflex or swelling that may occlude air flow and cause the patient to choke.

A dorsal anchor herein may be placed further posterior to the tongue than an inferior anchor as explained previously. A dorsal anchor may be positioned using the location of the lingual frenulum as an anatomical marker.

Embodiments of the invention include combinations of multiple dorsal anchors with one or more ventral anchors. Embodiments of the invention include combinations of multiple ventral anchors with one or more dorsal anchors.

Methods and devices disclosed herein may also be used in clinical situations to remove and/or reduce and/or prevent obstruction of the airway. Examples of such situations include, but are not limited to: emergency medicine, trauma medicine, protecting the airway in patients with altered consciousness, surgeries performed under anesthesia, etc. In one such example, method and devices disclosed herein may be used in patients post-operatively (e.g., after extubation, after general anesthesia, etc.). This may allow patients to lie more comfortably on their back in the post-operative period.

One or more components of any device 100 disclosed herein may be coated with or otherwise covered with one or more pharmaceutical substances. Examples of such substances include, but are not limited to: local anesthetics; dyes and other visual markers; anti-inflammatory substances; substances with a specific taste, etc. In one embodiment, the patient covers one or more components of a device 100 (e.g., suction anchor 122, an elongate member, etc.) with a local anesthetic for increased comfort.

Any of the device embodiments herein may comprise a secondary connector between components in addition to a primary connector. The secondary connector may be used to prevent components from physically separating if the primary connector breaks. For example, the embodiment shown in FIG. 4 may comprise a secondary connector (i.e., an additional connector) that connects first anchor 102 and second anchor 104. Thus, first anchor 102 and second anchor 104 are connected by the secondary connector and also by first elongate member 108. In another such example, the embodiment shown in FIG. 25 may comprise a secondary connector that connects suction anchor 122 and external anchor 118. Thus, suction anchor 122 and external anchor 118 are connected by the secondary connector and also by first elongate member 108. Such embodiments reduce the risk of broken components falling back into the patient's airway and causing acute airway obstruction. The patient may be instructed to discard the device if one or more components and/or connectors appear to be broken. The secondary connector may be physically separate from the primary connector. The secondary connector may be integrated with or connected to the primary connector. For example, the secondary connector may be a metal wire or mesh that is integrated with or otherwise connected to an elongate member. In any of the embodiments herein, the secondary connector may be made of a material with a different strength than a primary connector.

Although several embodiments of the invention are disclosed herein, various modifications (e.g., additions, deletions), combinations, etc. may be made to examples and embodiments herein without departing from the intended spirit and scope of the invention. Any component, anchor, connector, sensor, surgical tool, etc. of one device embodiment may be incorporated into or used for another device embodiment, unless to do so would render the resulting device embodiment unsuitable for this invention. For example, several device combinations are possible wherein the anchor of one embodiment disclosed herein is added to or used with a connector or elongate member of another embodiment disclosed herein unless doing so would render the resulting embodiment unsuitable for its intended use. Any suitable method disclosed herein may be used to attach or implant any of the devices disclosed herein. If method steps are disclosed in a particular order, the order of steps may be changed unless doing so would render the method embodiment unsuitable for its intended use. A method step described herein may be added to or used to replace a step of another method embodiment described herein. Various reasonable modifications, additions and deletions of this invention's examples or embodiments are to be considered equivalents of the described examples or embodiments.

As used in the description and claims, the singular form "a", "an" and "the" include both singular and plural references unless the context clearly dictates otherwise. For example, the term "anchor" may include, and is contemplated to include, a plurality of anchors. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating obstructive breathing disorders in a patient, the method comprising:
   providing an elongate implantable member having a first anchor and a second anchor;
   passing the elongate implantable member through a region of a tongue body of a tongue, wherein the first anchor and the second anchor do not pierce the tongue;
   reversibly coupling a flexible elongate member to the second anchor or the elongate implantable member, wherein the flexible elongate member is disposed superiorly to a dorsal surface of the tongue, and wherein the flexible elongate member comprises a coupling element for reversibly coupling to the second anchor or the elongate implantable member;
   applying a force to the flexible elongate member to generate tension on a portion of the tongue body; and
   adjusting a magnitude of the force,
   wherein at least a portion of the force is directed along an anterior direction, and
   wherein the force causes at least one of the following actions: an anterior displacement of a posterior portion of the tongue during sleep or reducing posterior displacement of a portion of the tongue during sleep.

2. The method of claim 1, wherein the flexible elongate member is coupled to a third anchor.

3. The method of claim 2, wherein the third anchor comprises an oral anchor or a dental anchor.

4. The method of claim 2, wherein the third anchor comprises a magnetic material.

5. The method of claim 1, wherein the coupling element is one of: a loop, lasso, hook, or clip.

6. The method of claim 1, further comprising advancing the tongue such that the elongate implantable member slides relative to the region of the tongue body.

7. The method of claim 1, further comprising removing the force by uncoupling the flexible elongate member from the second anchor or the elongate implantable member.

8. A method of treating obstructive breathing disorders in a patient, the method comprising:
   providing an elongate implantable member having a first anchor and a second anchor;
   passing the elongate implantable member through a region of a tongue body of a tongue, wherein one or both of the first anchor or the second anchor is physically separated by a distance from a tissue boundary of the tongue body, wherein the passing comprises positioning the first and second anchors in an anterior two thirds portion of the tongue body;
   advancing the tongue such that the elongate implantable member slides relative to the region of the tongue body;
   reversibly coupling a flexible elongate member to the second anchor or the elongate implantable member, wherein the flexible elongate member is disposed superiorly to a dorsal surface of the tongue;
   applying a force to the flexible elongate member to generate tension on a portion of the tongue body; and
   adjusting a magnitude of the force,
   wherein the force causes at least one of the following actions: an anterior displacement of a posterior portion of the tongue during sleep or reducing posterior displacement of a portion of the tongue during sleep.

9. The method of claim 8, wherein the passing comprises positioning the first and second anchors anterior to a circumvallate papillae of the tongue body.

10. The method of claim 8, wherein the passing comprises positioning the first and second anchors about 1 cm to about 3 cm posterior to a tip of the tongue body.

11. The method of claim 8, wherein the passing comprises positioning the first anchor on a dorsal region of the tongue body.

12. The method of claim 8, wherein the force is about 0.01N to about 5N.

13. The method of claim 8, further comprising reducing the force on the portion of the tongue body to zero force when the patient is at least partially upright or awake.

14. The method of claim 8, wherein the applying the force occurs when the patient is lying down or asleep.

15. The method of claim 8, further comprising simulating a sleep state for the patient and attaching a temporary anchor to the region of the tongue body before passing the elongate implantable member through the region of the tongue body.

16. The method of claim 8, further comprising generating a positive airway pressure to further create an anterior displacement force on one or more of: the portion of the tongue or a soft palate region.

17. The method of claim 8, wherein the flexible elongate member comprises one or more attachment regions for reversible attachment of the flexible elongate member to the second anchor or the elongate implantable member.

18. The method of claim 8, further comprising placing a temporary implant and allowing an initial healing period, wherein at least one of the first anchor or the second anchor is attached after the initial healing period.

19. A method of treating obstructive breathing disorders in a patient, the method comprising:
   providing an elongate implantable member having a first anchor and a second anchor;
   passing the elongate implantable member through a region of a tongue body of a tongue, wherein one or both of the first anchor or the second anchor is physically separated by a distance from a tissue boundary of the tongue body;
   advancing the tongue such that the elongate implantable member slides relative to the region of the tongue body;
   reversibly coupling a flexible elongate member to the second anchor or the elongate implantable member, wherein the flexible elongate member is disposed superiorly to a dorsal surface of the tongue, and wherein the flexible elongate member is connected to a third anchor;
   applying a force to the flexible elongate member to generate tension on a portion of the tongue body; and
   adjusting a magnitude of the force,
   wherein the force causes at least one of the following actions: an anterior displacement of a posterior portion of the tongue during sleep or reducing posterior displacement of a portion of the tongue during sleep.

20. The method of claim 19, wherein the third anchor is attached to a bodily region of the patient.

21. The method of claim 19, wherein a distance between the second anchor and the third anchor is adjustable across multiple levels.

22. The method of claim 19, wherein a length of the flexible elongate member between the second anchor and the third anchor is adjustable to adjust a displacement of the tongue during a patient sleep state.

23. The method of claim 19, wherein the force is a displacement force that is adjusted by methods comprising one or more of: changing an attachment region of the third anchor to an anatomy of the patient; changing a first physical parameter of the third anchor; changing a second physical parameter of the flexible elongate member; changing a first location or a first orientation of the third anchor; or changing a second location or a second orientation of the flexible elongate member.

24. The method of claim 19, wherein the third anchor comprises an oral anchor or a dental anchor.

25. The method of claim 19, wherein the third anchor comprises a magnetic material.

* * * * *